(12) United States Patent
Bryden et al.

(10) Patent No.: US 9,101,906 B2
(45) Date of Patent: Aug. 11, 2015

(54) POROUS BODY PRECURSORS, SHAPED POROUS BODIES, PROCESSES FOR MAKING THEM, AND END-USE PRODUCTS BASED UPON THE SAME

(71) Applicant: DOW TECHNOLOGY INVESTMENTS LLC, Midland, MI (US)

(72) Inventors: Todd R. Bryden, Midland, MI (US); Kevin E. Howard, Midland, MI (US); Peter C. Lebaron, Hope, MI (US); Sten A. Wallin, Midland, MI (US)

(73) Assignee: Dow Technology Investments LLC, Midland, MI (US)

( * ) Notice: Subject to any disclaimer, the term of this patent is extended or adjusted under 35 U.S.C. 154(b) by 0 days.

(21) Appl. No.: 14/226,575

(22) Filed: Mar. 26, 2014

(65) Prior Publication Data

US 2014/0206528 A1    Jul. 24, 2014

Related U.S. Application Data

(62) Division of application No. 12/988,317, filed as application No. PCT/US2009/042042 on Apr. 29, 2009, now Pat. No. 8,685,883.

(60) Provisional application No. 61/049,265, filed on Apr. 30, 2008.

(51) Int. Cl.
*B01J 23/00* (2006.01)
*B01J 23/02* (2006.01)
(Continued)

(52) U.S. Cl.
CPC ............... *B01J 27/055* (2013.01); *B01J 21/04* (2013.01); *B01J 23/50* (2013.01); *B01J 23/66* (2013.01); *B01J 23/688* (2013.01); *B01J 35/002* (2013.01); *B01J 35/1009* (2013.01); *B01J 35/1038* (2013.01); *B01J 35/1042* (2013.01); *B01J 37/0009* (2013.01); *B01J 37/0018* (2013.01); *B01J 37/0201* (2013.01);
(Continued)

(58) Field of Classification Search
CPC ................................. B01J 23/66; B01J 21/04
USPC ........................ 502/348, 355, 439; 423/600
See application file for complete search history.

(56) References Cited

U.S. PATENT DOCUMENTS

| 3,108,888 A | 10/1963 | Bugosh |
| 3,950,504 A | 4/1976 | Belding |

(Continued)

FOREIGN PATENT DOCUMENTS

| JP | 8103659 | 4/1996 |
| WO | 0187867 | 11/2001 |

(Continued)

*Primary Examiner* — Cam N. Nguyen
(74) *Attorney, Agent, or Firm* — Edward L. Brant; KSJLaw, LLC

(57) ABSTRACT

The present invention provides porous body precursors and shaped porous bodies. Also included are catalysts and other end-use products based upon the shaped porous bodies and thus the porous body precursors. Finally, processes for making these are provided. The porous body precursors comprise a precursor alumina blend capable of enhancing one or more properties of a shaped porous body based thereupon. The need to employ modifiers to achieve a similar result may thus be substantially reduced, or even avoided, and cost savings are thus provided, as well as savings in time and equipment costs.

1 Claim, 5 Drawing Sheets

(51) Int. Cl.

| | | |
|---|---|---|
| B01J 23/08 | (2006.01) | |
| B01J 23/48 | (2006.01) | |
| B01J 23/50 | (2006.01) | |
| B01J 21/04 | (2006.01) | |
| C01F 7/00 | (2006.01) | |
| B01J 27/055 | (2006.01) | |
| B01J 23/66 | (2006.01) | |
| B01J 23/68 | (2006.01) | |
| B01J 35/00 | (2006.01) | |
| B01J 35/10 | (2006.01) | |
| B01J 37/00 | (2006.01) | |
| B01J 37/02 | (2006.01) | |
| C07D 301/10 | (2006.01) | |

(52) U.S. Cl.
CPC ......... *B01J 37/0203* (2013.01); *B01J 37/0205* (2013.01); *B01J 37/0213* (2013.01); *C07D 301/10* (2013.01)

(56) References Cited

U.S. PATENT DOCUMENTS

| | | | |
|---|---|---|---|
| 3,992,329 | A | 11/1976 | Eaton |
| 4,036,784 | A | 7/1977 | Gembicki |
| 4,041,215 | A | 8/1977 | Kormanyos |
| 4,052,538 | A | 10/1977 | Eddy |
| 4,272,443 | A | 6/1981 | Titzenthaler |
| 4,428,863 | A | 1/1984 | Fry |
| 4,575,494 | A | 3/1986 | Young |
| 4,645,754 | A | 2/1987 | Tamura |
| 4,769,358 | A | 9/1988 | Kishimoto |
| 4,795,735 | A | 1/1989 | Liu |
| 5,077,256 | A | 12/1991 | Yamamoto |
| 5,100,859 | A | 3/1992 | Gerdes |
| 5,145,824 | A | 9/1992 | Buffum |
| 5,155,085 | A | 10/1992 | Hamano |
| 5,187,140 | A | 2/1993 | Thorsteinson |
| 5,380,697 | A | 1/1995 | Matusz |
| 5,418,202 | A | 5/1995 | Evans |
| 5,597,773 | A | 1/1997 | Evans |
| 5,703,253 | A | 12/1997 | Evans |
| 5,801,259 | A | 9/1998 | Kowaleski |
| 5,929,259 | A | 7/1999 | Lockemeyer |
| 6,174,511 | B1 | 1/2001 | Tsukada |
| 6,281,370 | B1 | 8/2001 | Shima |
| 6,313,325 | B1 | 11/2001 | Shima |
| 6,579,825 | B2 | 6/2003 | Lockemeyer |
| 6,787,656 | B2 | 9/2004 | Shima |
| 7,026,492 | B1 | 4/2006 | Kaminsky |
| 7,057,056 | B1 | 6/2006 | Qin |
| 7,067,187 | B2 | 6/2006 | Kawazu |
| 7,074,838 | B2 | 7/2006 | Colman |
| 7,102,047 | B2 | 9/2006 | Grubbs |
| 7,211,688 | B2 | 5/2007 | Clarke |
| 7,214,843 | B2 | 5/2007 | Beech |
| 7,238,817 | B1 | 7/2007 | Han |
| 7,256,149 | B2 | 8/2007 | Grey |
| 7,262,334 | B2 | 8/2007 | Schmidt |
| 7,271,117 | B2 | 9/2007 | Grey |
| 7,560,411 | B2 | 7/2009 | Yeates |
| 7,855,163 | B2 | 12/2010 | Liu |
| 2003/0191328 | A1 | 10/2003 | Jansen |
| 2004/0148868 | A1 | 8/2004 | Anderson |
| 2007/0111886 | A1 | 5/2007 | Serafin |
| 2009/0163362 | A1 | 6/2009 | Yener |
| 2010/0056816 | A1 | 3/2010 | Wallin |
| 2011/0136659 | A1 | 6/2011 | Allen |

FOREIGN PATENT DOCUMENTS

| | | |
|---|---|---|
| WO | 03072246 | 9/2003 |
| WO | 2005023417 | 3/2005 |
| WO | 2006028940 | 3/2006 |

POROUS BODY PRECURSORS, SHAPED POROUS BODIES, PROCESSES FOR MAKING THEM, AND END-USE PRODUCTS BASED UPON THE SAME

CROSS REFERENCE TO RELATED APPLICATIONS

This is a divisional application of U.S. patent application Ser. No. 12/988,317, filed Nov. 20, 2010, which is a 371 of international patent application No. PCT/US09/42042, filed Apr. 29, 2009, which claims benefit of U.S. provisional patent application Ser. No. 61/049,265, filed Apr. 30, 2008.

FIELD OF THE INVENTION

The present invention provides porous body precursors and shaped porous bodies. Also included are catalysts and other end-use products, such as filters, membrane reactors, composite bodies and the like, based upon the shaped porous bodies and thus the porous body precursors. Finally, processes for making these are provided.

BACKGROUND

Many facets of the practice of chemistry and/or chemical engineering can be reliant upon providing structures or surfaces capable of performing or facilitating separations or reactions and/or providing areas for such separations or reactions to take place. Such structures or surfaces are thus ubiquitous in many R&D and manufacturing settings. Although the desired physical and chemical properties of these shaped bodies can, and will, vary depending on the particular application, there are certain properties that are generally desirable in such shaped bodies regardless of the final application in which they will be utilized.

For example, such shaped bodies will desirably be of high purity and substantially inert so that the shaped bodies themselves will not participate in the separations or reactions taking place around, on or through them in a way that is undesired, unintended, or detrimental. For those shaped bodies for which it is desired to have the components being reacted or separated pass through, or diffuse into, the shaped body, a low diffusion resistance would be advantageous. In certain applications, the shaped bodies are desirably provided within a reaction or separation space, and so they are desirably of sufficient mechanical integrity to avoid being crushed, chipped or cracked during transport or placement. For those shaped bodies desirably utilized as reaction surfaces, high surface area and/or high porosity can be desired, to improve the loading and dispersion of the desired reactants, and also to provide enhanced surface area on which the reactions or separations can take place. Of course, in almost every application, lower cost materials are preferred.

Oftentimes, the desired properties of such shaped bodies can conflict with one another, and as a result, preparing shaped bodies where each desired property is maximized can be challenging. In efforts to meet these challenges, additives or binding agents, have been utilized. However, the use of such agents does not obviate the aforementioned challenge, as the use of such agents can improve one property at the expense of another. Furthermore, in addition to the cost of the agents themselves, the utilization of additives/binding agents to provide shaped bodies with desired properties, may require application of additional steps and the additional time and equipment expense that may be associated therewith.

Shaped porous bodies having desired properties optimized, or even maximized, would represent a vast improvement to the industry and would be expected to provide substantial benefits to end-use products and applications based thereupon. Processes for producing such shaped porous bodies, desirably without the addition of substantial additional expense in time, materials or equipment, would further leverage the benefit provided by such shaped porous bodies.

SUMMARY OF THE INVENTION

The present invention provides such improvements to shaped porous bodies and processes for producing them. Specifically, the present invention provides porous body precursors, upon which shaped porous bodies may be based, comprising a precursor alumina blend that enhances at least one property of a shaped porous body prepared from the porous body precursor. It has now surprisingly been discovered that by careful selection of at least two precursor aluminas, or at least two particle sizes of one or more precursor aluminas, utilized to prepare the precursor alumina blend, certain of the properties of the shaped porous bodies can be directed, so that reliance upon other additives to achieve similar property enhancements can be reduced, or even substantially eliminated. Even minor components of the precursor alumina blends can influence shaped porous body properties. As such, delicate control over shaped porous body properties is possible without excessive experimentation and/or additional material, time or equipment expense.

In a first aspect, the present invention provides a porous body precursor comprising a precursor alumina blend. The blend may comprise at least two secondary particle sizes of one precursor alumina, or, may comprise at least two precursor aluminas being of substantially of the same secondary particles size, or may comprise at least two precursor aluminas of differing secondary particle sizes. Preferably, the blend comprises at least two precursor aluminas having at least two secondary particle sizes. Desirably, the precursor alumina(s) utilized will have secondary particle sizes of from about 0.25 micrometers (µm) to about 100 µm, and in preferred embodiments, the precursor alumina blend will comprise at least 60 weight percent (wt %), or even at least 70 wt % of the larger of the at least two secondary particle sizes. The precursor aluminas may comprise any transition alumina precursor, transition alumina, alpha-alumina precursors, and as such, may comprise gibbsite, bayerite, and nordstrandite, boehmite, pseudo-boehmite, diaspore, gamma-alumina, delta-alumina, eta-alumina, kappa-alumina, chi-alumina, rho-alumina, theta-alumina, aluminum trihydroxides and aluminum oxide hydroxides.

In certain advantageous embodiments of the invention, the precursor aluminas, or secondary particles sizes of a single precursor alumina, selected for use in the blend may act synergistically to provide properties, or enhancements to properties, in the shaped porous bodies that are greater than the weighted average of the properties in shaped porous bodies prepared from any of the precursor alumina(s), or secondary particles sizes of a single precursor alumina, alone. Surprisingly, in certain embodiments of the invention, the enhancement can seemingly derive from a minor component of the precursor alumina blend. That is, the precursor alumina, or secondary particles size of a single precursor alumina, that provides the greater, e.g., surface area, when utilized to prepare a shaped porous body, when combined with a precursor alumina that provides a lower surface area in a shaped porous body based thereupon, can provide a shaped porous body having a surface area greater than the weighted average of the surface areas, even if the precursor alumina, or secondary particle size of the precursor alumina, that provides the greater surface area alone is present as a relatively minor component. The precursor alumina blend may thus comprise majority and minority components, and in these embodiments of the invention, the minority component may substantially dictate the property of the shaped porous body that is enhanced, the nature of the enhancement thereof, or both.

Because the precursor alumina blend is so effective at providing properties to, or enhancing properties of, shaped porous bodies prepared from porous body precursors comprising the blend, the use of additional modifiers or additives can be reduced or substantially avoided. A second aspect of the invention thus provides a shaped porous body prepared from a porous body precursor comprising a precursor alumina blend, wherein the blend enhances at least one property of the shaped porous body. Advantageously, the shaped porous body, and porous body precursor from which it is prepared, can be substantially free of additional additives and/or modifiers. The precursor alumina blend desirably enhances one or more of the surface area, aspect ratio, pore volume, median pore diameter, surface morphology, crush strength, and/or yield or failure stress of the shaped porous body, as compared to a shaped porous body prepared from a porous body precursor without the precursor alumina blend.

In a third aspect, processes for providing the shaped porous bodies are also provided, and comprise selecting a precursor alumina blend that will provide the shaped porous bodies with at least one enhanced property as compared to shaped porous bodies without the blend. The selected precursor aluminas, or particles sizes of a single precursor alumina, are combined to provide porous body precursors that are further processed to provide shaped porous bodies. The shaped porous bodies may be fluoride-affected if desired, and the same can be accomplished by exposing the porous body precursors and/or the shaped porous bodies to fluorine-containing species in gaseous form or in the form of one or more gaseous or liquid solutions.

Because the shaped porous bodies so produced are expected to have at least one property enhanced as compared to shaped porous bodies not comprising the precursor alumina blend, the inventive shaped porous bodies are expected to be advantageously employed in many end-use applications. In a fourth aspect, the present invention contemplates such use, and provides catalysts based upon the shaped porous bodies. More specifically, the catalysts comprise at least one catalytic species deposited on the shaped porous bodies, wherein the shaped porous bodies are prepared from porous body precursors comprising a precursor alumina blend. The catalytic species may comprise one or more metals, solid state compounds, molecular catalysts, enzymes or combinations of these. Desirably, the catalysts are suitable for the catalysis of the epoxidation of olefins, preferably alkylenes, more preferably alkylenes comprising from about 2 to about 6 carbon atoms. Most preferably, the catalysts are suitable for the catalysis of the epoxidation of ethylene or propylene, and in these embodiments of the invention, the catalytic species may preferably comprise a silver component. The catalyst may comprise any desired promoters, stabilizers, modifiers or additional additives, and combinations thereof.

Processes for making the catalysts are also provided and comprise selecting a precursor alumina blend that may provide shaped porous bodies based thereupon with at least one enhanced property relative to shaped porous bodies without the blend. The selected precursor aluminas, or the selected at least two secondary particles sizes of a single precursor alumina, are combined to provide porous body precursors that are further processed to provide shaped porous bodies. At least one catalytic species is then deposited on the shaped porous bodies to provide catalysts. Desirably, the catalysts are suitable to catalyze epoxidation reactions, and in particular, the epoxidation of olefins. In this embodiment of the invention, and although the catalytic species may be chosen from metals, solid state compounds, molecular catalysts, enzymes or combinations of these, the catalytic species preferably comprises a silver component. The shaped porous bodies preferably comprise alpha-alumina, and more preferably fluoride-affected alpha-alumina, which effect may be provided by exposure of the shaped porous bodies, or porous body precursors, to a fluorine-containing species, typically provided in gaseous form or in the form of one or more gaseous or liquid solutions.

DESCRIPTION OF THE DRAWINGS

The detailed description of the invention that follows may be further understood and/or illustrated when considered along with the attached drawings.

DETAILED DESCRIPTION OF THE INVENTION

Figure 1:
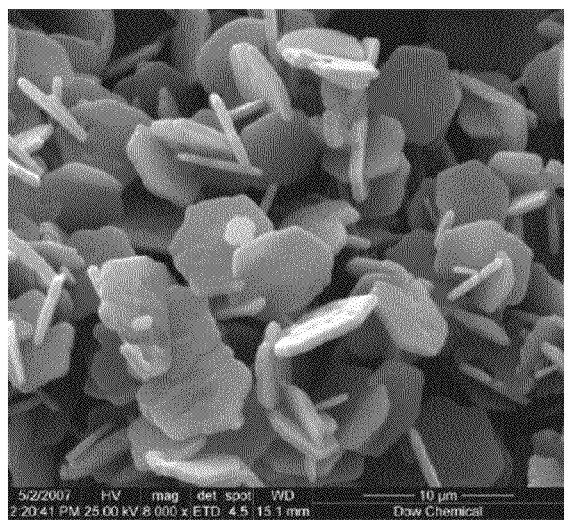
FIG. 1 depicts a scanning electron micrograph of a random sample of a comparative shaped porous body (shaped porous body ID C/comparative) produced in Example 1.
Figure 2:
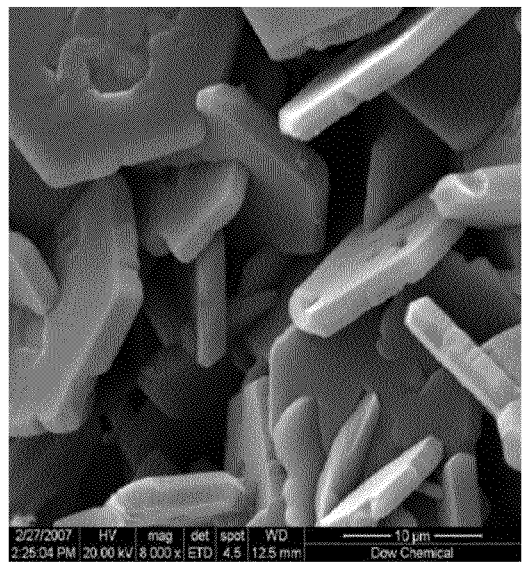
FIG. 2 depicts a scanning electron micrograph of a random sample of a comparative shaped porous body (shaped porous body ID D/comparative) produced in Example 1.
Figure 3:
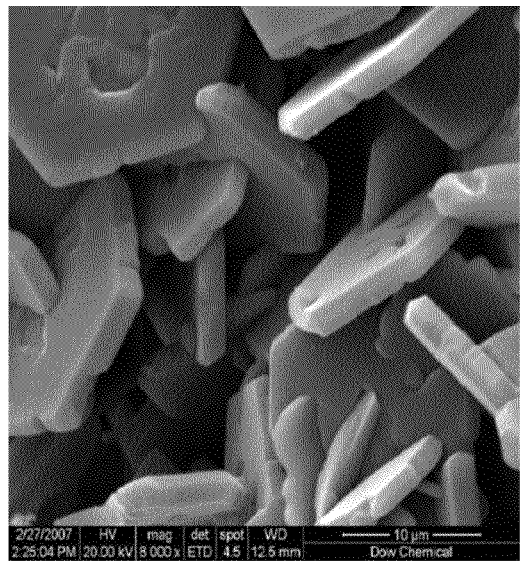
FIG. 3 depicts a scanning electron micrograph of a random sample of an inventive shaped porous body (shaped porous body ID E/1:1 Catapal B:Versal V-250) produced in Example 1.
Figure 4:
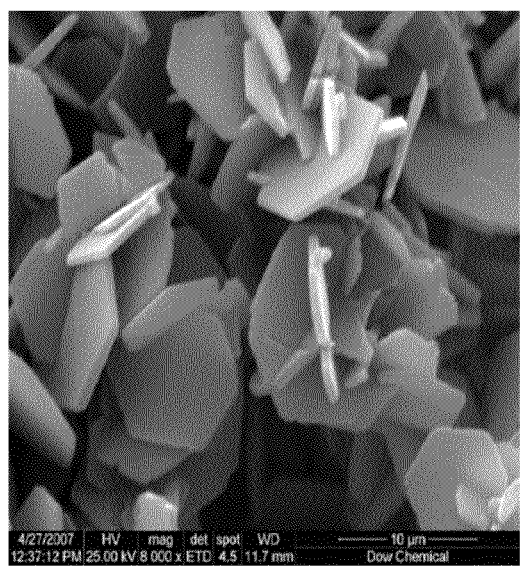
FIG. 4 depicts a scanning electron micrograph of a random sample of an inventive shaped porous bodies (shaped porous body ID F/3:1 Catapal B:Versal V-250) produced in Example 1.

The present specification provides certain definitions and methods to better define the present invention and to guide those of ordinary skill in the art in the practice of the present invention. Provision, or lack of the provision, of a definition for a particular term or phrase is not meant to bely any particular importance, or lack thereof, rather, and unless otherwise noted, terms are to be understood according to conventional usage by those of ordinary skill in the relevant art.

As used herein, the phrase 'porous body precursor' is defined as a solid which has been formed into a selected shape suitable for its intended use and in which shape it will be calcined or otherwise processed or reacted to provide a shaped porous body. The phrase, 'shaped porous body', in turn, is meant to indicate a solid which has been formed into a selected shape suitable for its intended use and has been further processed so as to have a porosity of greater than at least about 10%. As those of ordinary skill in the art are aware, shaped porous bodies may typically be comprised of many, typically thousands, tens of thousands, hundreds of thousands or even millions of smaller particles, and in the present application, it is the surface morphology or aspect ratio of these smaller particles that is observed or measured and referred to herein. As such, it is to be understood that when particular ranges are indicated as advantageous or desired for these measurements, or that a particular surface morphology has been observed, that these ranges may be based upon the measurement or observation of from about 1 to about 10 particles, and although it may generally be assumed that the majority of the particles may thus exhibit the observed morphology or be within the range of aspect ratio provided, that the ranges are not meant to, and do not, imply that 100% of the population, or 90%, or 80%, or 70%, or even 50% of the particles need to exhibit a surface morphology or possess an aspect ratio within this range.

The present invention provides porous body precursors, upon which shaped porous bodies may be based, comprising a blend of one or more precursor aluminas, i.e., the precursor alumina blend may comprise two secondary particle sizes of the same precursor alumina, that provide the shaped porous bodies with at least one enhanced property relative to shaped porous bodies that do not comprise the precursor alumina blend. Advantageously, the precursor alumina blend may be so effective at providing the desired property enhancement(s) that the use of additional modifiers to achieve the property enhancement(s) in question may be substantially reduced, or even entirely avoided. Material cost may thus be saved, as well as the time and equipment cost associated with adding such modifiers.

As used herein, the phrase 'precursor aluminas' is meant to include transition alumina precursors, transition aluminas, and other alpha-alumina precursors. 'Transition alumina precursors', in turn, are one or more materials that, upon thermal treatment, are capable of being at least partially converted to transition alumina. Transition alumina precursors include, but are not limited to, aluminum tri-hydroxides, such as gibbsite, bayerite, and nordstrandite, aluminum oxide hydroxides, such as boehmite, pseudo-boehmite and diaspore. 'Transition aluminas' are one or more aluminas other than alpha-alumina, which are capable of being at least partially converted to alpha-alumina under thermal treatment at 900° C. or greater. Transition aluminas possess varying degrees of crystallinity, and include, but are not limited to, gamma-alumina, delta-alumina, eta-alumina, kappa-alumina, chi-alumina, rho-alumina, and theta-alumina. 'Alpha-alumina precursor' means one or more materials capable of being transformed into alpha-alumina, including transition alumina precursors and transition aluminas. Further, as used herein, the phrase 'secondary particle' means an aggregate of primary particles of a precursor alumina. Primary particles of precursor aluminas are individual crystallites of the precursor aluminas and are typically on the order of nanometers in size and as such, are typically most accurately measured by x-ray diffraction. Secondary particles are aggregates of at least two of these primary particles, have sizes on the order of micrometers, and may be most accurately measured by light-scattering or sedimentation methods.

The selected blend of precursor aluminas will desirably enhance at least one property of a shaped porous body prepared from a porous body precursor comprising the blend. Any property desirably enhanced in such shaped porous bodies is within the scope of the present invention, and such properties may typically include surface area, aspect ratio, pore volume, median pore diameter, surface morphology, crush strength, yield or failure stress, calcined density, etc. 'Surface area', as used herein, refers to the surface area of the shaped porous bodies as determined by the BET (Brunauer, Emmett and Teller) method by nitrogen as described in the Journal of the American Chemical Society 60 (1938) pp. 309-316. 'Aspect ratio' means the ratio of the longest or major dimension to the smallest or minor dimension of the particles of which the shaped porous bodies are comprised, determined by examination of the scanning electron micrograph of the shaped porous body. 'Pore volume' (also, 'total pore volume' or 'porosity') means pore volume of the shaped porous body and is typically determined by mercury porosimetry. The measurements reported herein used the method described in Webb & Orr, Analytical Methods in Fine Particle Technology (1997), p. 155, using mercury intrusion to 60,000 psia using Micrometrics Autopore IV 9520, assuming 130° contact angle, 0.473 N/M surface tension of Hg. 'Median pore diameter' means the pore diameter corresponding to the point in the pore size distribution at which half of the cumulative pore volume of the shaped porous bode has been measured, and 'surface morphology' means the physical structure of the surface of the particles of which the shaped porous body is comprised, typically observed by scanning electron microscopy (SEM). Crush strength can be determined according to ASTM Method No. D-6175-98. Yield or failure stress can be determined according to ASTM C 1161-94.

Any combination of precursor aluminas, or particles sizes of a single precursor alumina, capable of providing a desired property to, or enhancing a property of, porous body precursors and/or shaped porous bodies is considered to be within the scope of the present invention. Advantageously, using a blend of precursor aluminas to provide a property, or an enhancement to a property, to shaped porous bodies prepared from porous body precursors comprising the blend can reduce, or even eliminate the use of other additives or modifiers to provide the same property or enhancement. Cost savings are thus provided, as well as time associated with experimentation to arrive at the additives or modifiers required to achieve the desired property and then adding the identified additives or modifiers to the porous body precursors. In particularly advantageous embodiments of the invention, the precursor aluminas selected for use in the blend may act synergistically to provide properties, or enhancements to properties, in the shaped porous bodies that are greater than the weighted average of the properties in shaped porous bodies prepared from either precursor alumina alone.

Further, it has now been surprisingly discovered that careful selection of the precursor aluminas, or particle sizes of one or more precursor alumina(s), utilized in the blend can provide delicate control over properties of the porous body precursors, shaped porous bodies and/or end-use products based upon the same. More particularly, it has now been discovered that precursor aluminas or particle sizes that provide a desired property when utilized to prepare porous body precursors, shaped porous bodies and/or end-use products alone, may be utilized in the precursor alumina blends of the present invention to provide the property, or the same property synergistically enhanced, in porous body precursors, shaped porous bodies and/or end-use products comprising the blend, even when the precursor alumina or particle size providing the property, or property enhancement, is present as only a minor component of the blend. While not wishing to be bound by any theory, it is thought that precursors aluminas, or particles sizes of a precursor alumina, that undergo phase transitions at lower temperatures, or at the same temperature more quickly, than other precursor aluminas or particle sizes utilized in the inventive precursor alumina blends will drive the properties of porous body precursors, shaped porous bodies, and/or end-use products comprising the precursor alumina blend.

As such, and for example, if a porous body precursor having an enhanced surface area is desired, but yet packing density is also desirably maintained or enhanced, a first precursor alumina or particle size that is capable of being processed into a shaped porous body that exhibits a relatively large surface area (as compared to shaped porous bodies prepared with other precursor aluminas) may be combined with a second precursor alumina expected to provide the desired packing density in the resulting shaped porous body. If the first precursor alumina undergoes a phase transition at lower processing temperatures than the second precursor alumina, according to the discovery that led to the present invention, the first precursor alumina may be utilized in the blend in a minor amount compared to the second, and yet shaped porous bodies based upon porous body precursors comprising this blend will be expected to not only exhibit an enhanced surface area, but a synergistically enhanced surface area relative to the surface area of shaped porous bodies based upon either precursor alumina alone.

Advantageously, the present invention thus provides a means for providing shaped porous bodies with desired properties without excessive experimentation, and potentially at great cost savings, i.e., it is at least possible, using the teachings of the present invention to provide properties to shaped porous bodies not only without the required use of additional modifiers or additives, but also to evaluate the cost of the precursor aluminas capable of providing the desired property, or enhancement to the property, and select the most cost effective precursor alumina capable of providing the desired outcome. Further, relatively minor amounts of the selected precursor aluminas may be effective at providing the desired property(ies), or property enhancement(s), thus providing the opportunity for further cost savings.

As mentioned above, the blend of precursor aluminas may comprise blends of one (in those embodiments of the invention wherein the blend comprises a blend of multiple secondary particle sizes of a single precursor alumina) or more transition alumina precursors, transition aluminas, or alpha-alumina precursors. The blend of precursor aluminas may thus comprise a blend of one or more gibbsites, bayerites, nordstrandites, boehmites, pseudo-boehmites, diaspores, gamma-aluminas, delta-aluminas, eta-aluminas, kappa-aluminas, chi-aluminas, rho-aluminas, theta-aluminas, aluminum trihydroxides and aluminum oxide hydroxides. Preferred blends comprise blends of one or more gibbsites and/or pseudo-boehmites.

As those of ordinary skill in the art are aware, the aforementioned transition alumina precursors, transition aluminas and alpha-alumina precursors may include numerous variants. Furthermore, these variants, conventionally differentiated by tradenames (e.g., Catapal B vs Catapal D, Versal V-250 vs Versal V-700) may differ only incrementally in chemical composition, physical and/or mechanical properties, such as density, pore volume, surface area, secondary particle size and primary, or crystallite, particle size. Yet, it has now been surprisingly discovered that precursor alumina blends comprising two or more variants of one type of transition alumina precursor, transition alumina, or alpha-alumina, or even two secondary particle sizes of a single variant, may yet provide a porous body precursor with properties synergistically enhanced relative to those comprising either variant, or either particle size of the variant, alone. As such, precursor alumina blends comprising two, e.g., pseudo-boehmite, gibbsite, boehmite, variants and porous body precursors, shaped porous bodies and end-use products based upon the same are considered to be within the scope of the invention. The nomenclature and properties of precursor aluminas are discussed at length in "Oxides and Hydroxides of Aluminum", Alcoa Technical Paper No. 19, Wefers and Misra, Alcoa Laboratories, 1987, commercially available for download at http://www.alcoa.com/globai/en/innovation/papers_patents/details/1987_paper_oxides_and_hydroxides.asp# and incorporated by reference herein for any and all purposes.

The precursor alumina blend may comprise any ratio of the selected precursor aluminas (or secondary particle sizes of a single precursor alumina) that provides an improvement to a property of shaped porous bodies prepared from porous body precursors comprising the blend. The selected precursor aluminas may be provided in substantially equal amounts, or, a majority of one may be provided. Exemplary ratios for blends comprising two precursor aluminas, or two secondary particle sizes of one precursor alumina, may thus range from 1:1, to as much as 100:1. Typically, ranges of from 1:1 to 10:1, or from 1:1 to 5:1 may be employed. If these are blends of two particles sizes, it may be preferable that the larger of the two particle sizes is present in the majority. In those preferred embodiments of the invention wherein the precursor alumina blend comprises more than two precursor aluminas, the ratio of aluminas may be such that the aluminas are present in relatively equal amounts, one or more are in a majority, one or more are in the minority, etc. Thus, suitable ratios for these blends may be from about 1:1:1 (or 1:1:1:1, etc.) to about 100:1:1 (or 100:1:1:1, etc) or from about 1:1:1 to about 10:1:1 (or 10:1:1:1, etc.), or from about 1:1:1 to about 5:1:1 (or 5:1:1:1, etc)

Surprisingly, in those embodiments of the invention wherein the porous body precursors have incorporated therein a precursor alumina blend comprising, e.g., two variants of a pseudo-boehmite (such as those pseudo-boehmite variants available under the tradenames Catapal® and Versal®) an improvement in the surface area of shaped porous bodies based thereupon may be provided that is not only synergistic in view of the surface area of shaped porous bodies comprising either variant alone, but may also derive from a relatively minor amount of the variant providing the greater surface area when utilized alone to provide shaped porous bodies. See Example 2, below.

The precursor alumina blend may further comprise a blend of multiple secondary particle sizes of one precursor alumina. It has now been surprisingly discovered that a mixture of large and small secondary particle sizes of one or more precursor aluminas, regardless of the particular aluminas used or their crystalline phase, can provide shaped porous bodies with enhanced properties. In these embodiments of the invention, it is not the particular secondary particle sizes that appear to be critical, but rather the ratio of the amounts of the secondary particle sizes to each other, and secondary particle size amount ratios, amount of larger secondary particles to amount of smaller secondary particles, of 1 to 0.01, or even 0.1 to 0.01, can provide enhanced properties to a shaped porous body prepared from a porous body precursor comprising a blend of precursor aluminas exhibiting that particle size relationship. In these embodiments of the invention, the larger secondary particles may advantageously make up at least about 60 wt %, or even up to 70 wt %, of the precursor alumina blend.

The porous body precursors may be entirely comprised of the precursor alumina blend, or, may comprise additional porous refractory structure or support materials, so long as whatever the additional porous refractory material(s) chosen, it doesn't substantially interfere with the ability of the precursor alumina blend to provide or enhance the desired property to the shaped porous body. That is, it may be possible for the precursor alumina blend to provide its beneficial effect when utilized in a porous body precursor in combination with other support materials. In addition to the precursor alumina blend, the porous body precursors may comprise, if desired, silicon carbide, silicon dioxide, zirconia, zirconium silicate, graphite, magnesia and various clays. If the porous body precursors desirably comprise other support materials, they are desirably present in relatively minor amounts, i.e., the precursor alumina blend will make up at least 50 wt %, or even 65 wt %, or up to about 75 wt %, of the porous body precursors. In preferred embodiments, the porous body precursors are comprised entirely of the precursor alumina blend.

The porous body precursors of the invention may comprise any other components, in any amounts, necessary or desired for processing, such as, e.g., water, acid, binders, pore formers, dopants, etc., of common knowledge to those of ordinary skill in the art of the production of shaped porous bodies for use as structures or supports. In those embodiments of the invention wherein the porous body precursors are intended for use in shaped porous bodies that will ultimately be used in catalytic applications, the porous body precursors may also contain precursor catalyst compounds that have elements that may desirably be incorporated onto the surface or into the lattice structure of the alpha-alumina particles that will be formed upon processing of the porous body precursors to form shaped porous bodies. Examples of compounds useful for forming these incorporated catalysts include inorganic and organic compounds that form catalysts such as metals, metal oxides, metal carbides and organo-metallic compounds.

The porous body precursors may also comprise other organic compounds (e.g., binders and dispersants, such as those described in *Introduction to the Principles of Ceramic Processing*, J. Reed, Wiley Interscience, 1988) to facilitate the shaping, or to alter the porosity, of the porous body precursors and/or shaped porous bodies. Pore formers (also known as burn out agents) are materials used to form specially sized pores in the shaped porous bodies by being burned out, sublimed, or volatilized. Pore formers are generally organic, such as ground walnut shells, granulated polyolefins, such as polyethylene and polypropylene, but examples of inorganic pore formers are known. The pore formers are usually added to the porous body precursor raw materials prior to shaping. During a drying or calcining step or during the conversion of the alpha-alumina precursor to alpha-alumina, the pore formers are burned out, sublimed, or volatilized.

The precursor alumina blends identified herein may prove so effective at imparting the desired properties, or enhancements to the property(ies), that the use of additional modifiers for this purpose may be reduced or substantially avoided. Nonetheless, if the same is desired or required, modifiers may also be added to the porous body precursor raw materials or the porous body precursors to change the chemical and/or physical properties of the shaped porous bodies or end-use products based upon the shaped porous bodies. If inclusion of the same is desired or required, any chosen modifier(s) can be added during any stage of the process, or at one or more steps in the process. For example, a metal oxide modifier can be added to the porous body precursor raw materials prior to, or after, the mixing/mulling step, prior to, or after, formation of the porous body precursors into formed porous body precursors, or before or after drying, or other thermal processing of the shaped porous bodies.

As used herein, "modifier" means a component other than the precursor alumina blend, and any other optional porous refractory material, added to a porous body precursor or shaped porous body to introduce desirable properties such as improved end-use performance. More particularly, modifiers can be inorganic compounds or naturally occurring minerals which are added in order to impart properties such as strength and, in some cases, change the surface chemical properties of the shaped porous bodies and/or end use products based thereupon. Non-limiting examples of such modifiers include zirconium silicate, see WO 2005/039757, alkali metal silicates and alkaline earth metal silicates, see WO 2005/023418, each of these being incorporated herein by reference for any and all purposes, as well as metal oxides, mixed metal oxides, for example, oxides of cerium, manganese, tin, and rhenium.

Whatever the raw materials selected for use in the porous body precursors, they are desirably of sufficient purity so that there are limited reactions between any of them. In particular, the precursor alumina blend should be of sufficient purity so that any impurities are not present in a quantity sufficient to substantially detrimentally impact the properties of the porous body precursors, shaped porous bodies and/or catalysts, i.e., any impurities are desirably limited to not more than 3 wt %, or even not more than 1.5 wt %, of the total weight of the porous body precursors.

The desired components of the porous body precursors, i.e., at least the precursor alumina blend, may be combined by any suitable method known in the art. Further, the precursor alumina blend and any other desired raw materials may be in any form, and combined in any order, i.e., the order of addition of the precursor alumina blend to the other raw materials, and the order of addition of the precursor aluminas themselves to the blend, is not critical. Examples of suitable techniques for combining the porous body precursor materials include ball milling, mix-mulling, ribbon blending, vertical screw mixing, V-blending, and attrition milling. The mixture may be prepared dry (i.e., in the absence of a liquid medium) or wet.

Once mixed, the porous body precursor materials may be formed by any suitable method, such as e.g., injection molding, extrusion, isostatic pressing, slip casting, roll compaction and tape casting. Each of these is described in more detail in *Introduction to the Principles of Ceramic Processing*, J. Reed, Chapters 20 and 21, Wiley Interscience, 1988, incorporated herein by reference in its entirety for any and all purposes. Suitable shapes for porous body precursors will vary depending upon the end use of the same, but generally can include without limitation pills, chunks, tablets, pieces, spheres, pellets, tubes, wagon wheels, toroids having star shaped inner and outer surfaces, cylinders, hollow cylinders, amphora, rings, Raschig rings, honeycombs, monoliths, saddles, cross-partitioned hollow cylinders (e.g., having at least one partition extending between walls), cylinders having gas channels from side wall to side wall, cylinders having two or more gas channels, and ribbed or finned structures. If cylinders, the porous body precursors may be circular, oval, hexagonal, quadrilateral, or trilateral in cross-section. In those embodiments of the invention wherein the porous body precursors are used to prepare shaped porous bodies intended for end use as catalysts, the porous body precursors may desirably be formed into a rounded shape, e.g., pellets, rings, tablets and the like, having diameters of from about 0.1 inch (0.25 cm) to about 0.8 inch (2 cm).

The porous body precursors so formed may then optionally be heated under an atmosphere sufficient to remove water, decompose any organic additives, or otherwise modify the porous body precursors prior to introduction into a kiln, oven, pressure-controlled reaction vessel or other container for any further required for processing into shaped porous bodies. Suitable atmospheres include, but are not limited to, air, nitrogen, argon, hydrogen, carbon dioxide, water vapor, those comprising fluorine-containing gases or combinations thereof.

Before or during calcination, and in those embodiments of the invention wherein the porous body precursors comprise one or more transition alumina precursors, transition aluminas, or other alpha-alumina precursors, the porous body precursors and/or shaped porous bodies may desirably be fluoride affected, as may be achieved by exposing the porous body precursors and/or shaped porous bodies to fluorine-containing species, as may be provided in gaseous form, in gaseous or liquid solution, or via the provision of solid fluorine-containing source operatively disposed relative to the porous body precursors and/or shaped porous bodies. For advantages provided in processing, any such fluoride effect may desirably be achieved via exposure of the porous body precursors and/or shaped porous bodies to one or more fluorine-containing species in gaseous form or in gaseous solution. The particulars of such gaseous fluoride affectation are described in copending, commonly assigned PCT application no. PCT/US2006/016437, the entire disclosure of which is hereby incorporated by reference herein for any and all purposes.

One preferred method of providing the fluoride effect to the porous body precursors or shaped porous bodies comprises heating a vessel containing porous body precursors comprising the precursor alumina blend to a temperature of from about 750° C. to about 1150° C., preferably from about 850° C. to about 1050° C. A fluorine-containing gas is then introduced into the vessel and can establish a partial pressure within the vessel of between about 1 torr and about 10,000 torr. The partial pressure may be 1, 100, 200, 300, 400, 500, 600, 700, 800, 900, 1000, 2500, 5000, 7500, or 10,000 torr or pressures in between. Preferred partial pressures are below about 760 torr. The porous body precursors are allowed to be in contact with the fluorine-containing gas for a time of about 1 minute to about 48 hours. The time may be 1 minute, 15 minutes, 30 minutes, 45 minutes, 1 hour, 90 minutes, 2 hours, 3 hours, 4 hours, 5 hours, 10 hours, 20 hours, 30 hours, 40 hours or about 48 hours or any amount of time in between. Shorter times for contacting the gas with the porous body precursors are preferred, with times of from about 30 minutes to about 90 minutes being particularly preferred. Of course, and as those of ordinary skill in the art can readily appreciate, the preferred combinations of time and temperature and/or pressure vary with the fluorine-containing gas used, the precursor alumina blend added to the porous body precursors, and any other components of the porous body precursors.

One particularly preferred method of providing a fluoride effect to porous body precursors comprising one or more transition alumina precursors, transition aluminas or other alpha-alumina precursors, comprises heating a vessel containing the porous body precursors to a first temperature in the range of about 850° C. to about 1150° C. prior to introducing the fluorine-containing gas and then heating to a second temperature greater than the first temperature and between about 950° C. and about 1150° C. after introducing the fluorine-containing gas. Desirably, in these embodiments of the invention, the first temperature is increased to the second temperature at a rate of about 0.2° C. to about 4° C. per minute. Whatever time and temperature combination utilized, at least 50% of the transition alumina precursors, transition aluminas or other alpha-alumina precursors are desirably converted to alpha-alumina platelets.

Another particular method for preparing porous body precursors suitable for the preparation of shaped porous bodies desirably comprising fluoride-affected alpha-alumina comprises selecting the precursor aluminas and mixing them to provide the precursor alumina blend, peptizing the precursor alumina blend with a mixture containing an acidic component and halide anions (preferably fluoride anions), forming (e.g., by extruding or pressing) the precursor alumina blend, and then drying and calcining the porous body precursors at temperatures between about 1000° C. and about 1400° C. for a time between about 45 minutes and about 5 hours to provide shaped porous bodies comprising fluoride-affected alpha-alumina.

Shaped porous bodies comprising alpha-alumina according to the invention will desirably have measured surface areas of at least about 0.5 $m^2/g$ (more preferably from about 0.7 $m^2/g$ to about 10 $m^2/g$), measured pore volumes of at least about 0.5 cc/g (more preferably from about 0.5 cc/g to about 2.0 cc/g), purity of at least about 90 percent alpha-alumina particles, preferably at least about 95 percent alpha-alumina particles, and more preferably at least about 99 weight percent alpha-alumina particles. However, the invention is not so limited and the shaped porous body may comprise any combination of transition alumina precursors, transition aluminas and alpha-alumina.

The shaped porous bodies also desirably having a median pore diameter from about 1 to about 50 microns. Further, the shaped porous bodies according to the invention will desirably be comprised largely of particles in the form of platelets have at least one substantially flat major surface having a lamellate or platelet morphology, at least 50 percent of which (by number) have a major dimension of less than about 50 microns. As used herein, the term "platelet" means that a particle has at least one substantially flat major surface, and that some of the particles have two, or sometimes more, flat surfaces. The "substantially flat major surface" referred to herein may be characterized by a radius of curvature of at least about twice the length of the major dimension of the surface.

Otherwise, the shaped porous bodies may comprise any suitable shape, as will depend upon the end use of the same. Like the porous body precursors, generally suitable shapes for the shaped porous bodies can include without limitation pills, chunks, tablets, pieces, spheres, pellets, tubes, wagon wheels, toroids having star shaped inner and outer surfaces, cylinders, hollow cylinders, amphora, rings, Raschig rings, honeycombs, monoliths, saddles, cross-partitioned hollow cylinders (e.g., having at least one partition extending between walls) cylinders having gas channels from side wall to side wall, cylinders having two or more gas channels, and ribbed or finned structures. If cylinders, the shaped porous bodies may be circular, oval, hexagonal, quadrilateral, or trilateral in cross-section. In those embodiments of the invention wherein the shaped porous bodies are used to prepare catalysts, the shaped porous bodies may desirably be formed into a rounded shape, e.g., pellets, rings, tablets and the like, having diameters of from about 0.1 inch (0.25 cm) to about 0.8 inch (2 cm).

Because of their advantageous, enhanced mechanical properties, the shaped porous bodies provided by the invention are particularly well suited for incorporation into many end-use applications. More particularly, shaped porous bodies of the invention can exhibit enhanced surface area, pore volume, median pore diameter, crush strength, and/or yield or failure stress, and be comprised of particles that may exhibit enhanced aspect ratios and/or surface morphologies and so are well suited for use as, e.g., catalyst supports, filters, membrane reactors and preformed bodies for composites. As used herein, "carrier" and "support" are interchangeable terms. A carrier provides surface(s) to deposit, for example, catalytic metals, metal oxides, or promoters that a components of a catalyst.

If used as catalyst supports, the shaped porous bodies may advantageously be used as supports for catalysts useful for the epoxidation of alkenes, partial oxidation of methanol to formaldehyde, partial selective oxidation of saturated hydrocarbons to olefins, selective hydroformylation of olefins, selective hydrogenations, selective hydrogenation of acetylenes in cracked hydrocarbon streams, selective hydrogenation of di-olefins in olefin-di-olefin-aromatic streams also known as pyrolysis gasoline, and selective reduction of $NO_x$ to $N_2$. Other catalytic applications for the present shaped porous bodies include as carriers for automotive exhaust catalysts for emissions control and as carriers for enzymatic catalysis. In addition to end-use applications as catalytic supports, the inventive shaped porous bodies may also be used for the filtration of materials from liquid or gas streams, see, e.g. Auriol, et al., U.S. Pat. No. 4,724,028. In these applications the shaped porous bodies may either be the discriminating material, or may be the carrier for the discriminating material. Other uses for the present shaped porous bodies include, but are not limited to, as packing for distillations and catalytic distillations.

Indeed, due to the numerous advantages imparted by the inventive shaped porous bodies to this particular end use, in one embodiment of the invention, the shaped porous body is used as the bases for a catalyst and these catalysts, as well as processes for making them, are also provided. Typically, such processes include at least depositing one or more catalytic species on the shaped porous bodies. Once deposited, the catalytic species can be bound directly on the surface of the shaped porous bodies of the invention, or, the catalytic species may be bound to a washcoat, i.e., another surface which has been applied to the surface of the shaped porous bodies. The catalytic species may also be covalently attached to a macromolecular species, such as synthetic polymer or a biopolymer such as a protein or nucleic acid polymers, which in turn, is bound either directly to the surface of the shaped porous bodies or a washcoat applied thereto. Further, a deposited catalytic species may reside on the surface of the shaped porous bodies, be incorporated into a lattice provided on the surface of the shaped porous bodies, or be in the form of discrete particles otherwise interspersed among the shape porous bodies.

If the shaped porous bodies are desirably used as supports for catalysts, any catalytic species may be deposited thereupon. Non-limiting examples of catalytic species that may advantageously be supported by the shaped porous bodies include metals, solid state compounds, molecular catalysts, enzymes and combinations of these.

Metals capable of exhibiting catalytic activity include noble metals, e.g. gold, platinum, rhodium, palladium, ruthenium, rhenium, and silver; base metals such as copper, chromium, iron, cobalt, nickel, zinc, manganese, vanadium, titanium, scandium, and combinations of these. Solid state compounds suitable for use as catalytic species include, but are not limited to, oxides, nitrides and carbides, and one particular example of a class of solid state compounds useful as a catalytic species are the perovskite-type catalysts that comprise a metal oxide composition, such as those described by Golden, U.S. Pat. No. 5,939,354, incorporated herein by reference. Exemplary molecular catalytic species include at least metal Schiff base complexes, metal phosphine complexes and diazaphosphacycles. Non-limiting examples of enzymes useful as catalytic species include lipases, lactases, dehalogenases or combinations of these, with preferred enzymes being lipases, lactases or combinations thereof.

The desired catalytic species may be deposited on the shaped porous bodies according to any suitable method, to provide catalysts according to the invention. Typically, metal catalytic species are conveniently applied by solution impregnation, physical vapor deposition, chemical vapor deposition or other techniques. Molecular and enzymatic catalysts may typically be provided onto the shaped porous bodies via covalent attachment directly to the shaped porous bodies, to a wash coat (such as silica, alumina, or carbon) or supported high surface area carbon (such as carbon nanotubes) applied thereto. Enzyme catalysts may also be supported by other supports known in the art, including the carbon nanofibers such as those described by Kreutzer, WO2005/084805A1, incorporated herein by reference, polyethylenimine, alginate gels, sol-gel coatings, or combinations thereof. Molecular catalyst may also be immobilized on the surface(s) of the shaped porous bodies by any of the immobilization generally known to those skilled in the art, such as attachment through silane coupling agents.

The amount of catalytic species may be any suitable amount depending on the particular catalytic species and application, and those of ordinary skill in the catalyst manufacturing art are well equipped to make this determination based upon their knowledge and information in the public arena. Very generally speaking then, typically, at least about 10 percent to essentially all of the shaped porous bodies may be coated with, or otherwise contain, catalytic species.

One particularly preferred class of catalysts according to the invention are those useful for the epoxidation of olefins. In olefin epoxidation, a feed containing an olefin and oxygen is contacted with a catalyst under epoxidation conditions, causing the olefin to react with oxygen to form an olefin oxide. The resulting product mix contains the olefin oxide, as well as any unreacted feed and other combustion products, such as carbon dioxide. The olefin oxide so produced may be reacted with water, alcohol or amines, for example, to produce diols, diol ethers or alkanolamines, respectively.

Ethylene glycol in particular is used in two significant applications: as a raw material for poly(ethylene terephthalate) for use in polyester fiber, film, and containers, and as an automotive antifreeze. Di-, tri-, and tetraethylene glycols are coproducts of ethylene glycol. Ethylene glycol can be produced by the (catalyzed or uncatalyzed) hydrolysis of ethylene oxide. Ethylene oxide hydrolysis proceeds with either acid or base catalysis or uncatalyzed in neutral medium. Acid-catalyzed hydrolysis activates the ethylene oxide by protonation for the reaction with water. Base-catalyzed hydrolysis results in considerably lower selectivity to ethylene glycol. A principal by-product is diethylene glycol and higher glycols, triethylene and tetraethylene glycols, are also produced. Ethylene glycol monoethers can be manufactured by reaction of an alcohol with ethylene oxide. Ethanolamine can be manufactured by the reaction of ethylene oxide with ammonia. See, e.g., U.S. Pat. No. 4,845,296, which is incorporated herein by reference.

One particular example of an olefin epoxidation of commercial importance is the epoxidation of alkylenes, or mixtures of alkylenes. Many references describe these reactions, representative examples of these being Liu et al., U.S. Pat. No. 6,511,938 and Bhasin, U.S. Pat. No. 5,057,481, as well as the Kirk-Othmer's Encyclopedia of Chemical Technology, 4th Ed. (1994) Volume 9, pages 915-959, all of which are incorporated by reference herein in their entirety for any and all purposes. Although the invention is not so limited, for purposes of simplicity and illustration, catalysts according to the invention useful in olefin epoxidations will be further described in terms of, and with reference to, the epoxidation of ethylene.

Catalysts are a very important factor in the commercial viability of such epoxidation reactions. The performance of catalysts in these reactions is typically evaluated on the basis of the catalysts' selectivity, activity, and stability during the epoxidation reactions. Selectivity is commonly understood to be the molar fraction of the converted olefin yielding the desired olefin oxide, while stability typically refers to how the selectivity or activity of the process during the time that a particular batch of catalyst is being used, i.e., as more olefin oxide is produced. Catalysts based upon the porous body precursors and shaped porous bodies of the present invention are expected to provide advantages in selectivity, activity and/or stability resulting from one or more property changes provided by inclusion of the precursor alumina blend in the porous body precursors.

In these embodiments of the invention in particular, a high purity shaped porous body is highly desirable. For these applications, a porous body precursor consisting essentially of the precursor alumina blend is highly desirable, and shaped porous bodies prepared from them will desirably comprise at least about 90 percent alpha-alumina platelets, more preferably at least about 95 percent alpha-alumina platelets, and even more preferably at least about 99 percent alpha-alumina platelets.

One method of obtaining such a high purity shaped porous body precursor is to extrude a mixture comprising a precursor alumina blend (e.g. Catapal B with Versal V-250 or Almatis S-3), an organic binder (e.g. methylcellulose), an organic lubricant (e.g. polyethylene glycol) and, optionally, an organic pore former (e.g. nut shell flour, polypropylene or polyethylene fibers or powders) followed by cutting, drying and debindering/calcining in air. In other epoxidation catalyst applications, and in addition to or further exemplary of the additional components or modifiers discussed hereinabove, shaped porous bodies prepared from porous body precursors comprising primarily the precursor alumina blend, but having minor silicate and/or other oxide components containing alkaline earth metal, transition metal, rare earth or main group elements may be highly desirable, particularly when these minor oxide components are in combination with silicon. Such shaped porous bodies are within the scope of this invention, and can readily be achieved by the processes provided herein, by adding the desired minor components as pure oxides or salts, or if desired as mixed oxides or salts, to the porous body precursors before shaping them to form the shaped porous bodies, or by adding the minor components via either solution or gas phase infiltration after forming the shaped porous bodies. Common additives for formation of minor phases giving improved catalyst performance in ethylene epoxidation reactions include silicates, alumino-silicates, borates, alkaline earth metal containing compounds, transition metal element-containing compounds, rare earth element-containing compounds, and main group element-containing compounds.

Shaped porous bodies suitable for end-use application as the basis for ethylene epoxidation catalysts according to the invention may take any of the shapes suitable for carriers or supports, discussed above. Conventional commercial fixed bed ethylene oxide reactors are typically in the form of a plurality of parallel elongated tubes (in a suitable shell) having an outer diameter of from about 1 inches to about 3 inches (2.5 to 7.5 cm) and a length of from about 15 feet to about 45 feet (4.5 to 13.5 m). For use in such fixed bed reactors, the shaped porous bodies will desirably be formed into a rounded shape, such as, for example, spheres, pellets, rings, tablets, and the like, having diameters from about 0.1 inch (0.25 cm) to about 0.8 inch (2 cm).

Catalysts according to this embodiment of the invention may be prepared by impregnating the inventive shaped porous bodies with a solution of one or more silver compounds, or otherwise depositing the silver throughout the pores of the shaped porous bodies and reducing the silver compound as is well known in the art. See for example, Liu, et al., U.S. Pat. No. 6,511,938 and Thorsteinson et al., U.S. Pat. No. 5,187,140, incorporated herein by reference.

Generally, the shaped porous bodies are impregnated with a catalytic amount of silver, which is any amount of silver capable of catalyzing the direct oxidation of, e.g., ethylene, with oxygen or an oxygen-containing gas to the corresponding alkylene oxide. Typically, the shaped porous bodies are impregnated with one or more silver compound solutions sufficient to allow the silver to be provided on the shaped porous bodies in an amount greater than about 5 percent, greater than about 10 percent, greater than about 15 percent, greater than about 20 percent, greater than about 25 percent, preferably, greater than about 27 percent, and more preferably, greater than about 30 percent by weight, based on the weight of the catalyst. Although the amount of silver utilized is not particularly limited, the amount of silver provided in connection with the shaped porous bodies may usually be less than about 70 percent, and more preferably, less than about 50 percent by weight, based on the weight of the catalysts.

Although silver particle size in the finished catalysts is important, the range is not narrow. A suitable silver particle size can be in the range of from about 10 angstroms to about 10,000 angstroms in diameter. A preferred silver particle size ranges from greater than about 100 angstroms to less than about 5,000 angstroms in diameter. It is desirable that the silver be relatively uniformly dispersed within, throughout, and/or on the shaped porous body.

As is known to those skilled in the art, there are a variety of known promoters, or materials which, when present in combination with particular catalytic materials, e.g., silver, benefit one or more aspects of catalyst performance or otherwise act to promote the catalyst's ability to make a desired product, e.g., ethylene oxide or propylene oxide. More specifically, and while such promoters in themselves are generally not considered catalytic materials, they typically may contribute to one or more beneficial effects of the catalysts' performance, for example enhancing the rate, or amount, of production of the desired product, reducing the temperature required to achieve a suitable rate of reaction, reducing the rates or amounts of undesired reactions, etc. Furthermore, and as those of ordinary skill in the art are aware, a material which can act as a promoter of a desired reaction can be an inhibitor of another reaction. For purposes of the present invention, a promoter is a material which has an effect on the overall reaction that is favorable to the efficient production of the desired product, whether or not it may also inhibit any competing reactions that may simultaneously occur.

There are at least two types of promoters—solid promoters and gaseous promoters. A solid promoter may conventionally be incorporated into the inventive catalysts prior to their use, either as a part of the shaped porous bodies, or as a part of the silver component applied thereto. Examples of well-known solid promoters for catalysts used to produce ethylene oxide include compounds of potassium, rubidium, cesium, rhenium, sulfur, manganese, molybdenum, and tungsten. Examples of solid promoter and their characteristics as well as methods for incorporating the promoters as part of the catalyst are described in Thorsteinson et al., U.S. Pat. No. 5,187,140, particularly at columns 11 through 15, Liu, et al., U.S. Pat. No. 6,511,938, Chou et al., U.S. Pat. No. 5,504,053, Soo, et al., U.S. Pat. No. 5,102,848, Bhasin, et al., U.S. Pat. Nos. 4,916,243, 4,908,343, and 5,059,481, and Lauritzen, U.S. Pat. Nos. 4,761,394, 4,766,105, 4,808,738, 4,820,675, and 4,833,261, all incorporated herein by reference in their entirety for any and all purposes.

Gaseous promoters, on the other hand, are gas-phase compounds or mixtures thereof which are introduced into a reactor, either alone or with other gas phase reactants, before or during the process desirably catalyzed. Gas phase promoters can desirably further enhance the performance of the catalyst, and may do so either alone, or may work in conjunction with one or more solid promoters. Halide-containing components, e.g., chlorine-containing components, may typically be employed as gaseous promoters in processes involving the epoxidation of alkylenes. See, for example, Law, et al., U.S. Pat. Nos. 2,279,469 and 2,279,470, each incorporated herein by reference in their entirety for any and all purposes.

Gaseous promoters capable of generating at least one efficiency-enhancing member of a redox half reaction pair may also be used, and one example of such a gaseous promoter would be any of those comprising a nitrogen-containing component. See, for example, Liu, et al., U.S. Pat. No. 6,511,938 particularly at column 16, lines 48 through 67 and column 17, line 28, and Notermann, U.S. Pat. No. 4,994,589, particularly at column 17, lines 10-44, each incorporated herein by reference in their entirety for any and all purposes. Alternatively, a suitable precursor compound may also be added such that the desired amount of the salt of a member of a redox-half reaction pair is formed in the catalyst under epoxidation conditions, especially through reaction with one or more of the gas-phase reaction components. The suitable range of concentrations of the precursor of the efficiency enhancing promoter is the same as for the salt. As used herein, the term "salt" does not indicate that the anion and cation components of the salt be associated or bonded in the solid catalyst, but only that both components be present in some form in the catalyst under reaction conditions.

Solid promoters are generally added as chemical compounds to the catalyst prior to its use. As used herein, the term "compound" refers to the combination of a particular element with one or more different elements by surface and/or chemical bonding, such as ionic and/or covalent and/or coordinate bonding. The term "ionic" or "ion" refers to an electrically charged chemical moiety; "cationic" or "cation" referring to a positively charged moiety and "anionic" or "anion" referring to a negatively charged moiety. The term "oxyanionic" or "oxyanion" refers to a negatively charged moiety containing at least one oxygen atom in combination with another element. An oxyanion is thus an oxygen-containing anion. It is understood that ions do not exist in vacuo, but are found in combination with charge-balancing counter ions when added as a compound to the catalyst.

Once incorporated into the catalyst, and/or during the reaction to make ethylene oxide, the specific form of the promoter on the catalyst may be unknown, and the promoter may be present without the counterion added during the preparation of the catalyst. For example, a catalyst made with cesium hydroxide may be analyzed to contain cesium but not hydroxide in the finished catalyst. Likewise, compounds such as alkali metal oxide, for example cesium oxide, or transition metal oxides, for example $MoO_3$, while not being ionic, may convert to ionic compounds during catalyst preparation or use. Oxyanions, or precursors to oxyanions, may be converted to a cationic or covalent form. In many instances, analytical techniques may not be sufficient to precisely identify the species present. The invention is not intended to be limited by the exact species that may ultimately exist on the catalyst during use and simply for the sake of ease of understanding, the solid promoters will be referred to in terms of cations and anions regardless of their form in the catalyst under reaction conditions.

The catalyst prepared on the inventive shaped porous bodies may contain alkali metal and/or alkaline earth metal as cationic promoters. Exemplary of the alkali metal and/or alkaline earth metals are lithium, sodium, potassium, rubidium, cesium, beryllium, magnesium, calcium, strontium and barium. Other cationic promoters include Group 3b metal ions including lanthanide series metals. In some instances, the promoter may comprise a mixture of cations, for example cesium and at least one other alkali metal, to obtain a synergistic efficiency enhancement as described in U.S. Pat. No. 4,916,243, herein incorporated by reference. Note that references to the Periodic Table herein shall be to that as published by the Chemical Rubber Company, Cleveland, Ohio, in CRC Handbook of Chemistry and Physics, 46th Edition, inside back cover.

The concentration of the alkali metal promoters in the finished catalyst, if desirably included therein, is not narrow and may vary over a wide range. The optimum alkali metal promoter concentration for a particular catalyst will be dependent upon performance characteristics, such as catalyst efficiency, rate of catalyst aging and reaction temperature. More particularly, the concentration of alkali metal (based on the weight of cation, for example cesium) in the finished catalysts of the present invention may vary from about 0.0005 to 1.0 wt. %, preferably from about 0.005 to 0.5 wt. %. The preferred amount of cation promoter deposited on or present on the surface of the shaped porous body or catalyst generally lies between about 10 ppm and about 4000 ppm, preferably between about 15 ppm and about 3000 ppm, and more preferably between about 20 ppm and about 2500 ppm by weight of cation calculated on the total shaped porous body material. Amounts between about 50 ppm and about 2000 ppm may be most preferred.

In those embodiments of the invention wherein the alkali metal cesium is employed as a promoter in combination with other cations, the ratio of cesium to any other alkali metal and alkaline earth metal salt(s), if used, to achieve desired performance is not narrow and may vary over a wide range. The ratio of cesium to the other cation promoters may vary from about 0.0001:1 to 10,000:1, preferably from about 0.001:1 to 1,000:1. Preferably, cesium comprises at least about 10, more preferably, about 20 to 100, percent (weight) of the total added alkali metal and alkaline earth metal in those catalyst embodiments comprising cesium as a promoter.

Examples of anionic promoters which may be employed in catalysts according to the present invention include halides, for example fluorides and chlorides, and oxyanions of elements other than oxygen having an atomic number of 5 to 83 of Groups 3b to 7b and 3a to 7a of the Periodic Table. One or more of the oxyanions of nitrogen, sulfur, manganese, tantalum, molybdenum, tungsten and rhenium may be preferred for some applications. Preferred anionic promoters suitable for use in the catalysts of this invention comprise, by way of example only, oxyanions such as sulfate, $SO_4^{-2}$, phosphates, for example, $PO_4^{-3}$, titanates, e.g., $TiO_3^{-2}$, tantalates, for example, $Ta_2O_6^{-2}$, molybdates, for example, $MoO_4^{-2}$, vanadates, for example, $V_2O_4^{-2}$, chromates, for example, $CrO_4^{-2}$, zirconates, for example, $ZrO_3^{-2}$, polyphosphates, manganates, nitrates, chlorates, bromates, borates, silicates, carbonates, tungstates, thiosulfates, cerates and the like. Halides may also be utilized as anion promoters in the catalysts of the present invention, and include, e.g., fluoride, chloride, bromide and iodide.

It is well recognized that many anions have complex chemistries and may exist in one or more forms, for example, orthovanadate and metavanadate; and the various molybdate oxyanions such as $MoO_4^{-2}$, and $Mo_7O_{24}^{-6}$ and $Mo_2O_7^{-2}$. The oxyanions may also include mixed metal-containing oxyanions including polyoxyanion structures. For instance, manganese and molybdenum can form a mixed metal oxyanion. Similarly, other metals, whether provided in anionic, cationic, elemental or covalent form may enter into anionic structures.

When the promoter comprises rhenium, the rhenium component can be provided in various forms, for example, as the metal, as a covalent compound, as a cation or as an anion. The rhenium species that provides the enhanced efficiency and/or activity is not certain and may be the component added or that generated either during preparation of the catalyst or during use as a catalyst. Examples of rhenium compounds include the rhenium salts such as rhenium halides, the rhenium oxyhalides, the rhenates, the perrhenates, the oxides and the acids of rhenium. However, the alkali metal perrhenates, ammonium perrhenate, alkaline earth metal perrhenates, silver perrhenates, other perrhenates and rhenium heptoxide may also be used. Rhenium heptoxide, $Re_2O_7$, when dissolved in water, hydrolyzes to perrhenic acid, $HReO_4$, or hydrogen perrhenate. Thus, for purposes of this specification, rhenium heptoxide can be considered to be a perrhenate, that is, $ReO_4$. Similar chemistries can be exhibited by other metals such as molybdenum and tungsten.

Promoters comprising manganese may also be utilized in catalysts according to the invention. The manganese species that provides the enhanced activity, efficiency and/or stability is not certain and may be the component added or that generated either during catalyst preparation or during use as a catalyst. Manganese components believed to be capable of acting as catalytic promoters, include, but are not limited to, manganese acetate, manganese ammonium sulfate, manganese citrate, manganese dithionate, manganese oxalate, manganous nitrate, manganous sulfate, and manganate anion, for example permanganate anion, and the like. To stabilize the manganese component in certain impregnating solutions, it may be necessary to add a chelating compound such as ethylenediaminetetraacetic acid (EDTA) or a suitable salt thereof.

Anionic promoters may be provided in any suitable promoting amount, and are typically providing in amounts ranging from about 0.0005 wt % to 2 wt %, preferably from about 0.001 wt % to 0.5 wt % based on the total weight of the catalyst. When used, the rhenium component may often be provided in amounts of at least about 1 ppm, or up to at least about 5 ppm, or even in amounts of between about 10 ppm to about 2000 ppm, or between about 20 ppm and 1000 ppm, calculated as the weight of rhenium based on the total weight of the catalyst.

The promoters for catalyst employing the present invention may also be of the type comprising at least one efficiency-enhancing salt of a member of a redox-half reaction pair which is employed in an epoxidation process in the presence of a gaseous nitrogen-containing component capable of forming a gaseous efficiency-enhancing member of a redox-half reaction pair under reaction conditions. The term "redox-half reaction" is defined herein to mean half-reactions like those found in equations presented in tables of standard reduction or oxidation potentials, also known as standard or single electrode potentials, of the type found in, for instance, "Handbook of Chemistry", N. A. Lange, Editor, McGraw-Hill Book Company, Inc., pages 1213-1218 (1961) or "CRC Handbook of Chemistry and Physics", 65th Edition, CRC Press, Inc., Boca Raton, Fla., pages D155-162 (1984). The term "redox-half reaction pair" refers to the pairs of atoms, molecules or ions or mixtures thereof which undergo oxidation or reduction in such half-reaction equations.

Further, the phrase "redox-half reaction pairs" is used herein to include those members of the class of substance which provide the desired performance enhancement, rather than a mechanism of the chemistry occurring. Preferably, such compounds, when associated with the catalyst as salts of members of a half reaction pair, are salts in which the anions are oxyanions, and preferably are oxyanions of a polyvalent atom; that is, the atom of the anion to which oxygen is bonded is capable of existing, when bonded to a dissimilar atom, in different valence states. As used herein, the term "salt" does not indicate that the anion and cation components of the salt must be associated or bonded in the solid catalyst, but only that both components be present in some form in the catalyst under reaction conditions. Potassium is the preferred cation, although sodium, rubidium and cesium may also be utilized, and the preferred anions are nitrate, nitrite and other anions capable of forming nitrate anions under epoxidation conditions. Preferred salts include $KNO_3$ and $KNO_2$, with $KNO_3$ being most preferred.

The amount of any such salt of a member of a redox-half reaction pair utilized in catalysts according to the invention may vary widely, and generally speaking, any amount may be utilized that enhances the efficiency of the reaction to be catalyzed. The precise amount will vary depending upon such variables as the gaseous efficiency-enhancing member of a redox-half reaction used and concentration thereof, the concentration of other components in the gas phase, the amount of silver contained in the catalyst, the surface area of the support, the process conditions, for example space velocity and temperature, and morphology of support. Alternatively, a suitable precursor compound may also be added such that the desired amount of the salt of a member of a redox-half reaction pair is formed in the catalyst under epoxidation conditions, especially through reaction with one or more of the gas-phase reaction components. Generally, however, a suitable range of concentration of the added efficiency-enhancing salt, or precursor thereof, calculated as cation, is about 0.01 to about 5%, preferably about 0.02 to about 3%, by weight, based on the total weight of the catalyst. Most preferably the salt is added in an amount of about 0.03 to about 2 wt. %.

The preferred gaseous efficiency-enhancing members of redox-half reaction pairs are compounds containing an element capable of existing in more than two valence states, preferably nitrogen, oxygen, or combinations of these. Most preferably, the gaseous component capable of producing a member of a redox-half reaction pair under reaction conditions is a generally a nitrogen-containing gas, such as for example nitric oxide, nitrogen dioxide and/or dinitrogen tetroxide, hydrazine, hydroxylamine or ammonia, nitroparaffins (for example, nitromethane), nitroaromatic compounds (for example nitrobenzene), N-nitro compounds, and nitriles (for example, acetonitrile).

The amount of nitrogen-containing gaseous promoter useful in catalysts according to the invention can vary widely, and is generally that amount that is sufficient to enhance the performance, e.g., the activity and/or efficiency, of the catalyst in the reaction to be catalyzed. The concentration of the nitrogen-containing gaseous promoter is determined by the particular efficiency-enhancing salt of a member of a redox-half reaction pair used and the concentration thereof, the particular alkene undergoing oxidation, and by other factors including the amount of carbon dioxide in the inlet reaction gases. For example, U.S. Pat. No. 5,504,053 discloses that when the nitrogen-containing gaseous promoter is NO (nitric oxide), a suitable concentration is from about 0.1 ppm to about 100 ppm, by volume, of the gas stream.

Although in some cases it may be preferred to employ members of the same half-reaction pair in the reaction system, that is, both the efficiency-enhancing salt promoter associated with the catalyst and the gaseous promoter in the feedstream, as, for example, with a preferred combination of potassium nitrate and nitric oxide, this is not necessary in all cases to achieve satisfactory results. Other combinations, such as $KNO_2/N_2O_3$, $KNO_3/NO_2$, $KNO_3/N_2O_4$, $KNO_2/NO$, $KNO_2/NO_2$ may also be employed in the same reaction system. In some instances, the salt and gaseous members may be found in different half-reactions which represent the first and last reactions in a series of half-reaction equations of an overall reaction.

As alluded to hereinabove, whatever the solid and/or gaseous promoter(s) employed in the present catalysts, they are desirably provided in a promoting amount. A "promoting amount" of a certain promoter refers to an amount of that promoter that works effectively to provide an improvement in one or more of the properties of a catalyst comprising the promoter relative to a catalyst not comprising said promoter. Examples of catalytic properties include, inter alia, operability (resistance to run-away), selectivity, activity, conversion, stability and yield. The promoting effect provided by the promoters can be affected by a number of variables such as for example, reaction conditions, catalyst preparative techniques, surface area and pore structure and surface chemical properties of the support, the silver and co-promoter content of the catalyst, the presence of other cations and anions present on the catalyst. The presence of other activators, stabilizers, promoters, enhancers or other catalyst improvers can also affect the promoting effects.

It is understood by one skilled in the art that one or more of the individual catalytic properties may be enhanced by the "promoting amount" while other catalytic properties may or may not be enhanced or may even be diminished. It is further understood that different catalytic properties may be enhanced at different operating conditions. For example, a catalyst having enhanced selectivity at one set of operating conditions may have enhanced activity and the same selectivity at a different set of operating conditions. Those of ordinary skill in the art may likely intentionally change the operating conditions in order to take advantage of certain catalytic properties even at the expense of other catalytic properties and will make such determinations with an eye toward maximizing profits, taking into account feedstock costs, energy costs, by-product removal costs and the like.

Whatever their amounts, it is desirable that the silver and one or more solid promoters be relatively uniformly dispersed on the shaped porous bodies. A preferred procedure for depositing silver catalytic material and one or more promoters comprises: (1) impregnating a shaped porous body according to the present invention with a solution comprising a solvent or solubilizing agent, silver complex and one or more promoters, and (2) thereafter treating the impregnated shaped porous body to convert the silver compound and effect deposition of silver and the promoter(s) onto the exterior and interior pore surfaces of the shaped porous bodies. Silver and promoter depositions are generally accomplished by heating the solution containing shaped porous bodies at elevated temperatures to evaporate the liquid within the shaped porous bodies and effect deposition of the silver and promoters onto the interior and exterior surfaces of the shaped porous bodies.

Impregnation of the shaped porous bodies is the preferred technique for silver deposition because it utilizes silver more efficiently than coating procedures, the latter being generally unable to effect substantial silver deposition onto the interior surfaces of the shaped porous bodies. In addition, coated catalysts are more susceptible to silver loss by mechanical abrasion. Whatever the manner of impregnation, the silver and one or more promoters may be impregnated simultaneously, or the promoters may be impregnated prior to, or after, the silver impregnation, and multiple impregnations may be used in order to achieve the desired weight percent of the silver and/or promoters on the shaped porous carrier.

The silver solution used to impregnate the shaped porous bodies may desirably be comprised of a silver compound in a solvent or complexing/solubilizing agent, such as any of the many silver solutions known in the art. The particular silver compound employed may be chosen, for example, from among silver complexes, silver nitrate, silver oxide, or silver carboxylates, such as silver acetate, oxalate, citrate, phthalate, lactate, propionate, butyrate and higher fatty acid salts. Silver oxide complexed with amine is a preferred form of silver for use in preparing catalysts according to the present invention.

A wide variety of solvents or complexing/solubilizing agents may be employed to solubilize silver to the desired concentration in the impregnating solution. Among those suitable for this purpose include, but are not limited to, lactic acid, ammonia, alcohols (such as ethylene glycol), amines and aqueous mires of amines. For example, $Ag_2O$ can be dissolved in a solution of oxalic acid and ethylenediamine to provide a concentration of approximately 30% by weight. Vacuum impregnation of such a solution onto a shaped porous body having a porosity of approximately 0.7 cc/g typically may result in a catalyst comprising approximately 25 wt % silver, based on the entire weight of the catalyst.

Accordingly, if it is desired to obtain a catalyst having a silver loading of greater than about 25 wt % or about 30 wt % or more, it would generally be necessary to subject the shaped porous bodies to at least two or more sequential impregnations of silver, with or without promoters, until the desired amount of silver is deposited on the shaped porous bodies. In some instances, the concentration of the silver salt may desirably be higher in the latter impregnation solutions than in the first. In other instances, approximately equal amounts of silver are deposited during each impregnation. Often, to effect equal deposition in each impregnation, the silver concentration in the subsequent impregnation solutions may need to be greater than that in the initial impregnation solutions. In other instances, a greater amount of silver is deposited on the shaped porous bodies in the initial impregnation than that deposited in subsequent impregnations. Each of the impregnations may be followed by roasting or other procedures to render the silver insoluble.

Well known methods can be employed to analyze the particular amounts of silver and/or solid promoters deposited onto the shaped porous bodies. The skilled artisan may employ, for example, material balances to determine the amounts of any of these deposited components. Alternatively, any suitable analytical technique for determining elemental composition, such as X-ray fluorescence (XRF), may be employed to determine the amounts of the deposited components.

The present invention is applicable to epoxidation reactions in any suitable reactor, for example, fixed bed reactors, continuous stirred tank reactors (CSTR), and fluid bed reactors, a wide variety of which are well known to those skilled in the art and need not be described in detail herein. The desirability of recycling unreacted feed, employing a single-pass system, or using successive reactions to increase ethylene conversion by employing reactors in series arrangement can also be readily determined by those skilled in the art. The particular mode of operation selected is usually dictated by process economics. Conversion of olefin (alkylene), preferably ethylene, to olefin oxide, preferably ethylene oxide, can be carried out, for example, by continuously introducing a feed stream containing alkylene (e.g., ethylene) and oxygen or an oxygen-containing gas to a catalyst-containing reactor at a temperature of from about 200° C. to about 300° C., and a pressure which may vary between about 5 atmospheres (506 kPa) and about 30 atmospheres (3.0 MPa), depending upon the mass velocity and productivity desired. Residence times in large-scale reactors are generally on the order of from about 0.1 seconds to about 5 seconds. Oxygen may be supplied to the reaction in an oxygen-containing stream, such as, air or as commercial oxygen, or as oxygen-enriched air. The resulting alkylene oxide, preferably, ethylene oxide, is separated and recovered from the reaction products using conventional methods.

The following examples are set forth for the purpose of illustrating the invention; but these examples are not intended to limit the invention in any manner. One skilled in the art will recognize a variety of substitutions and modifications of the examples that will fall within the scope of the invention.

EXAMPLE 1

A. Preparation of Porous Body Precursors Comprising a Precursor Alumina Blend, and Shaped Porous Bodies Based Thereupon Porous body precursors comprising a precursor alumina blend and having the shape of about ¼" O.D. 3/32" I.D. ¼" long rings are prepared in the following manner. Catapal D (hereinafter 'CatD'), Catapal B (hereinafter 'CatB') and Versal V-250 (hereinafter 'V-250') are obtained from UOP LLC, Des Plaines Ill., and Almatis S3 (hereinafter 'A-S3') is obtained from Almatis GmbH, Frankfurt Germany. Particle size range is approximately from about 0.1 micron to 100 microns, most preferably between about 1 micron and 50 microns.

An extrudable paste is prepared by mix mulling the desired precursor alumina blend with A-4M methocel (Dow Chemical Company, Midland Mich. USA), oleic acid (VWR Scientific Products, West Chester Pa. USA) and water and the mixture is ram extruded to form bars with a thickness of about 1.5 mm, width of about 11 mm and a length of about 70 mm. The bars are dried at 60° C. for 72 hours and then calcined at 700° C. for 4 hours. After drying, the shaped porous bodies are fired so that the transitional alumina is converted to platelet alpha-alumina using the gas phase reaction process described in co-pending, commonly assigned PCT application serial no. PCT/US2006/016437, incorporated herein by reference.

More particularly, to convert the alumina to alpha-alumina and thus provide shaped porous bodies, the formed porous body precursors are loaded into a reactor consisting of a 6 inch diameter by 22 inch long alumina tube, the reactor is evacuated, and heated to a temperature of about 840° C. After being at these conditions overnight, the reactor is filled with Freon HFC-134a to a pressure of 300 torr and held for three hours. The reactor is ramped at 2° C./min to 960° C. and held at 960° C. for 2 more hours. The reactor is cooled at 2° C./min and purged with nitrogen three times.

Properties for the inventive shaped porous bodies so produced, including the levels of the transition alumina, transition alumina precursor, or alpha-alumina precursor in each, and comparative shaped porous bodies are given in Table I. The shaped porous bodies made using 100% Almatis S3 have little post-calcination strength and cannot be handled to measure properties, and thus, these shaped porous bodies are not included in Table I. Inventive shaped porous body B is compared to comparative shaped porous body A and inventive shaped porous bodies E and F are compared to comparative shaped porous bodies C and D.

As shown, shaped porous bodies incorporating one embodiment of a precursor alumina blend according to the invention (SPB ID B) exhibit an increase of >100% in yield stress, with a decrease in pore volume of less than 10%, as compared to shaped porous bodies without the precursor alumina blend (SPB ID A). Other shaped porous bodies according to the invention exhibit increases in crush strength, while maintaining or increasing surface area (SPB ID's E and F) relative to shaped porous bodies without the precursor alumina blend (SPB ID's C and D). Surprisingly, even as a minority component, the Versal component has a large impact on the surface area of shaped porous body ID's E and F. And, in the instance of the shaped porous body ID F, the 1:1 CatB:V-250 blend, it would appear that the two precursor aluminas act synergistically to provide a surface area in the shaped porous bodies prepared from the same that is not provided in shaped porous bodies prepared with either precursor alumina alone (SPB ID's C and D). Scanning electron micrographs of a random sample of the comparative shaped porous bodies C and D and inventive shaped porous bodies E and F are also provide at FIGS. 1-5, respectively.

TABLE I

Properties of Shaped Porous Bodies (SPBs)

| SPB ID | Failure Stress (MPa) | Pore Volume (cc/g) | Surface Area (m²/g) | Crush Strength (lb/mm) |
|---|---|---|---|---|
| A<br>100 wt % CatD<br>(FIG. 5)<br>(Comparative) | 4 ± 1 | 0.54 | 0.45 | — |
| B<br>70:30 wt %<br>CatD:A-S3 | 9 ± 2 | 0.50 | 0.67 | 2.7 |
| C<br>100 wt % V-250<br>(FIG. 1)<br>(Comparative) | — | 0.77 | 1.3 | 1.0 |
| D<br>100 wt % CatB<br>(FIG. 2)<br>(Comparative) | — | 0.70 | 0.5 | 1.6 |
| E<br>3:1<br>(FIG. 3)<br>CatB:V-250 | — | 0.60 | 1.3 | 2.3 |
| F<br>1:1<br>(FIG. 4)<br>CatB:V-250 | — | 0.77 | 2.0 | 2.0 |

TABLE I-continued

Properties of Shaped Porous Bodies (SPBs)

Figure 6:
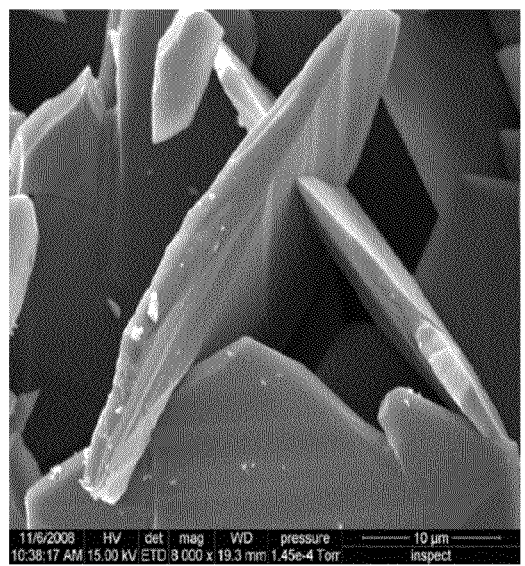
FIG. 6 depicts a scanning electron micrograph of a random sample of a comparative shaped porous body (shaped porous body ID G/comparative) produced in Example 1.
Figure 7:
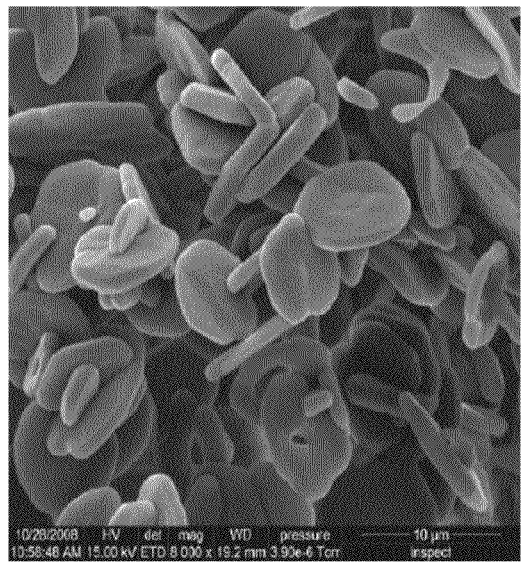
FIG. 7 depicts a scanning electron micrograph of a random sample of an inventive shaped porous body (shaped porous body ID H/1:1 Catapal 200:Versal V-250) produced in Example 1.
Figure 8:
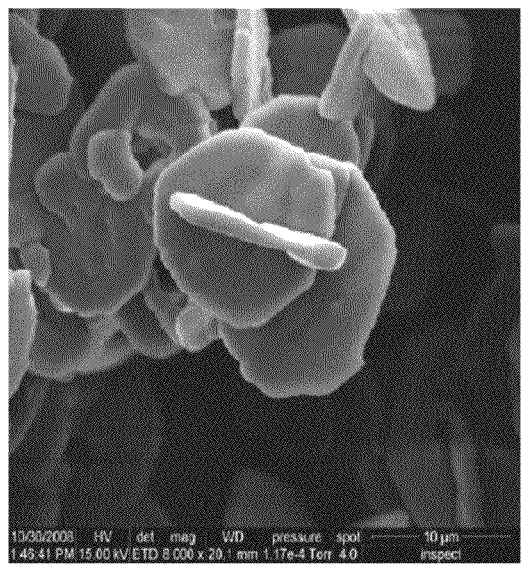
FIG. 8 depicts a scanning electron micrograph of a random sample of an inventive shaped porous bodies (shaped porous body ID I/3:1 Catapal D:Versal V-250) produced in Example 1.
Figure 9:
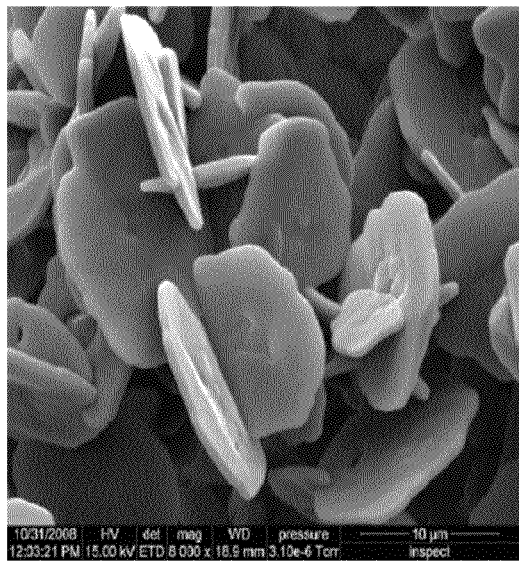
FIG. 9 depicts a scanning electron micrograph of a random sample of an inventive shaped porous bodies (shaped porous body ID J/4:1 Catapal B:Versal V-250) produced in Example 1.

| SPB ID | Failure Stress (MPa) | Pore Volume (cc/g) | Surface Area (m²/g) | Crush Strength (lb/mm) |
|---|---|---|---|---|
| G<br>100 wt % Cat200<br>(FIG. 6)<br>(Comparative) | — | — | — | — |
| H<br>1:1<br>(FIG. 7)<br>Cat200:V-250 | — | — | — | — |
| I<br>3:1<br>(FIG. 8)<br>CatD:V-250 | — | — | — | — |
| J<br>4:1<br>(FIG. 9)<br>CatB:V-250 | — | — | — | — |

Figure 5:
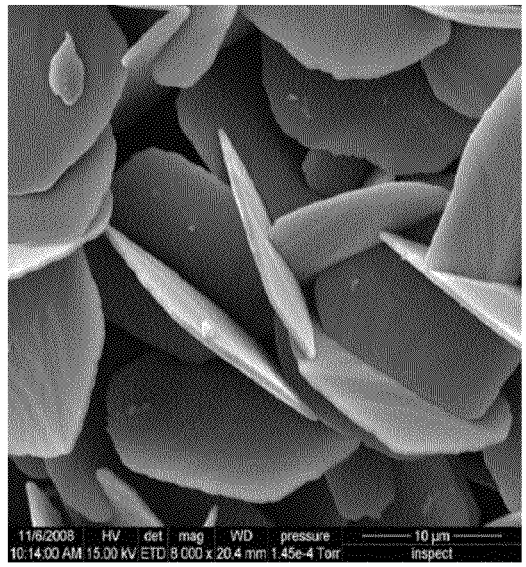
FIG. 5 depicts a scanning electron micrograph of a random sample of a comparative shaped porous body (shaped porous body ID A/comparative) produced in Example 1.

Although the mechanical properties listed in Table 1 were not determined for shaped porous body ID's G-J, SEM photographs of these SPB's are also provided at FIGS. 6-9. As can be seen by comparing FIG. 6 (Sample G, 100 wt % Cat200) and FIG. 1 (Sample C, 100 wt % V-250) to FIG. 7 (Sample H, 1:1 Cat200:V-250). FIG. 5 (Sample A, 100 wt % CatD) and FIG. 1 (Sample C, 100 wt % V-250) to FIG. 8 (Sample I, 3:1 CatD:V-250), and FIG. 2 (Sample D, 100 wt % CatB) and FIG. 1 (Sample C, 100 wt % V-250) to FIG. 9 (Sample J, 4:1 CatB:V-250), even though V-250 is present as a minority component, the platelet morphology of the blends appears to be directed by the Versal V-250, as the pure Catapals are shown to convert to large, 10-40 micron diameter platelets in the absence of a structure directing additive.

B. Catalyst Preparation Based Upon the Shaped Porous Body of IA

Catalysts will be prepared based upon the shaped porous bodies prepared according to part I.A as follows. The shaped porous bodies prepared in part I.A will be vacuum impregnated with a first impregnation silver solution typically containing about 30 weight percent (wt %) silver oxide, from about 15 wt % to about 20 wt % oxalic acid, from about 15 wt % to about 20 wt % ethylenediamine, from about 3 wt % to about 8 wt % monoethanolamine, and from about 25 to about 30 wt % distilled water. The first impregnation solution will typically be prepared by (1) mixing the ethylenediamine (high purity grade) with the distilled water; (2) slowly adding the oxalic acid dihydrate (reagent grade) to the aqueous ethylenediamine solution such that the temperature of the solution does not exceed about 40° C., (3) slowly adding the silver oxide, and (4) adding the monoethanolamine (Fe and Cl free).

The shaped porous bodies will be impregnated in an appropriately sized glass or stainless steel cylindrical vessel which will be equipped with suitable stopcocks for impregnating the shaped porous bodies under vacuum. A suitable separatory funnel will be inserted through a rubber stopper into the top of the impregnating vessel. The impregnating vessel containing the shaped porous bodies will be evacuated to approximately 1-2" mercury absolute for from about 10 to about 30 minutes, after which the impregnating solution will slowly be added to the shaped porous bodies by opening the stopcock between the separatory funnel and the impregnating vessel. After all the solution is emptied into the impregnating vessel (~15 seconds), the vacuum will be released and the pressure returned to atmospheric. Following addition of the solution, the shaped porous bodies will remain immersed in the impregnating solution at ambient conditions for 5 to 30 minutes, and thereafter be drained of excess solution for from about 10 minutes to about 30 minutes to provide catalysts.

The silver-impregnated catalysts will be roasted as follows to effect reduction of silver on the catalyst surface. The catalysts will be spread out in a single layer on stainless steel wire mesh trays, placed on a stainless steel belt (spiral weave) and transported through a 2"×2" square heating zone for from about 1 minute to about 5 minutes, or equivalent conditions for a larger belt operation. The heating zone will be maintained at from about 450° C. to about 550° C. by passing hot air upward through the belt and the catalysts at the rate of from about 250 to about 275 standard cubic feet per hour (SCFH). After being roasted in the heating zone, the catalysts will be cooled in the open air to room temperature and weighed.

Next, the silver-impregnated catalysts will be vacuum impregnated with a second silver impregnation solution containing both the silver oxalate amine solution and the catalyst promoters. The second impregnation solution will be composed of all of the drained solution from the first impregnation plus a fresh aliquot of the first solution, or a new solution will be used. The promoters, added with stirring in order to solubilize them, will be added in sufficient amounts to reach the desired target levels on the finished catalysts. Promoters and stabilizers may include neat cesium sulfate, cesium hydroxide solution, manganous (II) nitrate solution and diammonium EDTA solution. Two equivalents of diammonium EDTA will be added with the manganese promoter in order to increase the stability of the manganese-containing ion in the impregnation solution. The impregnation, draining and roasting steps for this second impregnation will be carried out analogously to the first impregnation.

The twice-impregnated finished catalysts will again be weighed, and based upon the weight gain of the catalysts in the second impregnation, the weight percent of silver and the concentration of the promoters will be calculated. The promoter target levels will be adjusted to shaped porous body surface area. The expected results of these calculations are provided in Table II. Due at least in part to the enhanced properties provided to the shaped porous bodies by the precursor alumina blend, catalysts prepared from the shaped porous bodies are expected to be capable of being impregnated with greater amounts of silver and the exemplary chosen promoters. Further, due to the synergistically enhanced surface area of shaped porous body F provided by the precursor alumina blend, it is expected that greater amounts of silver and exemplary chosen promoters will be able to be deposited thereupon relative to even inventive catalyst E.

TABLE II

Expected Catalyst Properties

| Catalyst ID | Ag (wt %) | Cs (ppm) | Mn (ppm) | SO₄ (ppm) |
|---|---|---|---|---|
| A<br>100 wt % CatD<br>(Comparative) | ~33 | ~450 | ~65 | ~80 |

TABLE II-continued

Expected Catalyst Properties

| Catalyst ID | Ag (wt %) | Cs (ppm) | Mn (ppm) | SO$_4$ (ppm) |
|---|---|---|---|---|
| B<br>70:30 wt %<br>CatD:A-S3 | Comp value A + ≥0.5 | Comp value A + ≥20 | Comp value A + ≥5 | Comp value A + ≥15 |
| C<br>100 wt % V-250<br>(Comparative) | ~33 | ~450 | ~65 | ~80 |
| D<br>100 wt % CatB<br>(Comparative) | ~33 | ~450 | ~65 | ~80 |
| E<br>3:1<br>CatB:V-250 | Comp value C or<br>D + ≥0.5 | Comp value C or<br>D + ≥20 | Comp value C or<br>D + ≥5 | Comp value C or<br>D + ≥15 |
| F<br>1:1<br>CatB:V-250 | Comp value C or<br>D + ≥1.0 | Comp value C or<br>D + ≥30 | Comp value C or<br>D + ≥10 | Comp value C or<br>D + ≥20 |
| G<br>100 wt % Cat200<br>(FIG. 6)<br>(Comparative) | ~33 | ~450 | ~65 | ~80 |
| H<br>1:1<br>(FIG. 7)<br>Cat200:V-250 | Comp value C or<br>G + ≥0.5 | Comp value C or<br>G + ≥20 | Comp value C or<br>G + ≥5 | Comp value C or<br>G + ≥15 |
| I<br>3:1<br>(FIG. 8)<br>CatD:V-250 | Comp value A or<br>C + ≥0.5 | Comp value A or<br>C + ≥20 | Comp value A or<br>C + ≥5 | Comp value A or<br>C + ≥15 |
| J<br>4:1<br>(FIG. 9)<br>CatB:V-250 | Comp value C or<br>D + ≥0.5 | Comp value C or<br>D + ≥20 | Comp value C or<br>D + ≥5 | Comp value C or<br>D + ≥15 |

C. Use of Inventive and Comparative Catalysts Prepared According to I.B to Catalyze Ethylene Epoxide Reactions A single-pass tubular reactor made of 0.25 inch OD stainless steel (wall thickness 0.035 inches) will be used for catalyst testing. The inlet conditions of the reactor that will be used are shown in Table III.

TABLE III

Ethylene Epoxidation Process Conditions

| Component | Oxygen Process Conditons-I<br>Mole % |
|---|---|
| Ethylene | 30.0 |
| Oxygen | 8.0 |
| Ethane | 0.5 |
| Carbon Dioxide | 6.5 |
| Nitrogen | Balance of gas |
| Parts per million Ethyl Chloride | 3.5 |
| Type of Reactor | Tube |
| Amount of Catalyst | 0.5 g |
| Total Outlet Flow Rate | 120 cc/min |

The pressure will be maintained constant at about 200 psig for the tube reactors. Ethyl chloride concentration will be adjusted to maintain maximum efficiency. Temperature (° C.) needed to produce 1.7 mole % ethylene oxide and catalyst efficiency (selectivity) at the outlet are typically measured and regarded as indicative of catalyst performance.

The catalyst test procedure is as follows: Approximately 5 g of catalyst will be crushed with a mortar and pestle, and then sieved to 30/50 U.S. Standard mesh. From the meshed material, 0.5 g will be charged to the reactor. Glass wool will be used to hold the catalyst in place. The reactor tube will be fitted into a heated brass block which has a thermocouple placed against it. The block will be enclosed in an insulated box. Feed gas will be passed over the heated catalyst at a pressure of 200 psig. The reactor flow will be adjusted and recorded at standard pressure and room temperature. Measurements of efficiency/selectivity and activity/temperature will be made under steady state conditions.

Table IV shows the expected temperature and selectivity as the total cumulative production of the reactor increases over time. Inventive catalyst B is compared to comparative catalyst A and inventive catalysts E and F are compared to comparative catalysts C and D. Due at least in part to the enhanced properties provided to the shaped porous bodies by the precursor alumina blend, catalysts prepared from the shaped porous bodies are expected to be capable of being impregnated with greater amounts of silver and the exemplary chosen promoters, and thus are expected to provide enhanced performance over time. Further, due to the synergistically enhanced surface area of shaped porous body F provided by the precursor alumina blend, it is expected that greater amounts of silver and exemplary chosen promoters will be able to be deposited thereupon relative to even inventive catalyst E, and thus that the performance of catalyst F will be enhanced relative to comparative catalysts C and D, and perhaps even inventive catalyst E.

TABLE IV

| Catalyst | A 100 wt % CatD (Comp) | B 70:30 CatD:A-S3 | C 100 wt % V-250 (Comp) | D 100 wt % CatB (Comp) | E 3:1 CatB:V-250 | F 1:1 CatB:V-250 | G 100 wt % Cat200 (Comp) | H 1:1 Cat200:V-250 | I 3:1 CatD:V-250 | J 4:1 CatB:V-250 |
|---|---|---|---|---|---|---|---|---|---|---|
| Day 18 | | | | | | | | | | |
| Selectivity (%) | ~82 | Comp value + ≥0.1 | ~82 | ~82 | Comp value + ≥0.1 | Comp value + ≥0.1 | ~82 | Comp value + ≥0.1 | Comp value + ≥0.1 | Comp value + ≥0.1 |
| Temperature (C.) | ~243 | Comp value − ≥0.1 | ~243 | ~243 | Comp value − ≥0.1 | Comp value − ≥0.1 | ~243 | Comp value − ≥0.1 | Comp value − ≥0.1 | Comp value − ≥0.1 |
| Day 27 | | | | | | | | | | |
| Selectivity (%) | ~82 | Comp value + ≥0.1 | ~82 | ~82 | Comp value + ≥0.1 | Comp value + ≥0.1 | ~82 | Comp value + ≥0.1 | Comp value + ≥0.1 | Comp value + ≥0.1 |
| Temperature (C.) | 247.7 | Comp value − ≥0.1 | | | Comp value − ≥0.1 | Comp value − ≥0.1 | | Comp value − ≥0.1 | Comp value − ≥0.1 | Comp value − ≥0.1 |
| Day 59 | | | | | | | | | | |
| Selectivity (%) | ~82 | Comp value + ≥0.1 | ~82 | ~82 | Comp value + ≥0.1 | Comp value + ≥0.1 | ~82 | Comp value + ≥0.1 | Comp value + ≥0.1 | Comp value + ≥0.1 |
| Temperature (C.) | 252.3 | Comp value − ≥0.1 | | | Comp value − ≥0.1 | Comp value − ≥0.1 | | Comp value − ≥0.1 | Comp value − ≥0.1 | Comp value − ≥0.1 |

EXAMPLE 2

A. Preparation of Porous Body Precursors Comprising a Precursor Alumina Blend, and Shaped Porous Bodies Based Thereupon Porous body precursors comprising a precursor alumina blend and having the shape of about ¼" O.D. ³⁄₃₂" I.D. ¼" long rings will be prepared in the following manner. Catapal D (hereinafter 'CatD', a pseudo-boehmite), Catapal B (hereinafter 'CatB', a pseudo-boehmite) and Versal V-250 (hereinafter 'V-250', a pseudo-boehmite) will be obtained from UOP LLC, Des Plaines, Ill., USA, and Alphabond 300 (hereinafter A-300, a gibbsite) will be obtained from Alcoa, Pittsburgh, Pa. USA.

An extrudable paste will be prepared by mix mulling the desired precursor alumina blend with A-4M methocel (Dow Chemical Company, Midland Mich. USA), oleic acid (VWR Scientific Products, West Chester Pa. USA) and water and the mixture will be ram extruded to form bars with a thickness of about 1.5 mm, width of about 11 mm and a length of about 70 mm. The bars will be dried at about 60° C. for about 72 hours and then calcined at about 700° C. for about 4 hours. After drying, the shaped porous bodies are fired so that the transitional alumina is converted to platelet alpha-alumina using the gas phase reaction process described in co-pending, commonly assigned PCT application serial no. PCT/US2006/016437, incorporated herein by reference.

More particularly, to convert the alumina to alpha-alumina and thus provide shaped porous bodies, the formed porous body precursors will be loaded into a reactor consisting of a 6 inch diameter by 22 inch long alumina tube, the reactor will be evacuated, and heated to a temperature of about 840° C. After being at these conditions overnight, the reactor will be filled with Freon HFC-134a to a pressure of about 300 torr and held for about three hours. The reactor will be ramped at about 2° C./min to about 960° C. and held at about 960° C. for approximately 2 more hours. The reactor will then be cooled at about 2° C./min and purged with nitrogen three times.

Expected properties for the inventive shaped porous bodies so produced, including the levels of the transition alumina, transition alumina precursor, or alpha-alumina precursor in each, and comparative shaped porous bodies are given in Table V. More specifically, as indicated in Table V, it is expected that shaped porous bodies comprising precursor alumina blends of one precursor alumina having two or more particle sizes (Sample ID's L and M), comprising blends of particles sizes of Catapal D) are expected to exhibit enhancements to failure stress, pore volume and surface area, as are shaped porous bodies comprising precursor alumina blends of three or four different precursor aluminas (Samples N, O and P).

TABLE V

Expected Properties of Shaped Porous Bodies (SPBs)

| SPB ID | Failure Stress (MPa) | Pore Volume (cc/g) | Surface Area (m²/g) |
|---|---|---|---|
| K 100 wt % CatD (Comparative) | 4 ± 1 | 0.54 | 0.45 |
| L 100 wt % CatD 70:30 Particle size 50µ:1µ | Comp Value + ≥1 | Comp Value + ≥0.05 | Comp Value + ≥0.5 |
| M 100 wt % CatD 40:30:30 Particle size 100µ:50µ:1µ | Comp Value + ≥1 | Comp Value + ≥0.05 | Comp Value + ≥0.5 |
| N 1:1:1 CatD:CatB:A-300 | Comp Value + ≥1 | Comp Value + ≥0.05 | Comp Value + ≥0.5 |
| O 3:1:1 CatD:CatB:V-250 | Comp Value + ≥1 | Comp Value + ≥0.05 | Comp Value + ≥0.5 |
| P 1:1:1:1 CatD:CatB:V-250:A-300 | Comp Value + ≥1 | Comp Value + ≥0.05 | Comp Value + ≥0.5 |

B. Catalyst Preparation Based Upon the Shaped Porous Bodies of 2A

Catalysts will be prepared based upon the shaped porous bodies prepared according to part 2.A as follows. The shaped porous bodies prepared in part 2.A will be vacuum impregnated with a first impregnation silver solution typically containing about 30 weight percent (wt %) silver oxide, from about 15 wt % to about 20 wt % oxalic acid, from about 15 wt % to about 20 wt % ethylenediamine, from about 3 wt % to about 8 wt % monoethanolamine, and from about 25 to about 30 wt % distilled water. The first impregnation solution will typically be prepared by (1) mixing the ethylenediamine (high purity grade) with the distilled water; (2) slowly adding the oxalic acid dihydrate (reagent grade) to the aqueous ethylenediamine solution such that the temperature of the solution does not exceed about 40° C., (3) slowly adding the silver oxide, and (4) adding the monoethanolamine (Fe and Cl free).

The shaped porous bodies will be impregnated in an appropriately sized glass or stainless steel cylindrical vessel which will be equipped with suitable stopcocks for impregnating the shaped porous bodies under vacuum. A suitable separatory funnel will be inserted through a rubber stopper into the top of the impregnating vessel. The impregnating vessel containing the shaped porous bodies will be evacuated to approximately 1-2" mercury absolute for from about 10 to about 30 minutes, after which the impregnating solution will slowly be added to the shaped porous bodies by opening the stopcock between the separatory funnel and the impregnating vessel. After all the solution is emptied into the impregnating vessel (~15 seconds), the vacuum will be released and the pressure returned to atmospheric. Following addition of the solution, the shaped porous bodies will remain immersed in the impregnating solution at ambient conditions for 5 to 30 minutes, and thereafter be drained of excess solution for from about 10 minutes to about 30 minutes to provide catalysts.

The silver-impregnated catalysts will be roasted as follows to effect reduction of silver on the catalyst surface. The catalysts will be spread out in a single layer on stainless steel wire mesh trays, placed on a stainless steel belt (spiral weave) and transported through a 2"×2" square heating zone for from about 1 minute to about 5 minutes, or equivalent conditions for a larger belt operation. The heating zone will be maintained at from about 450° C. to about 550° C. by passing hot air upward through the belt and the catalysts at the rate of from about 250 to about 275 standard cubic feet per hour (SCFH). After being roasted in the heating zone, the catalysts will be cooled in the open air to room temperature and weighed.

Next, the silver-impregnated catalysts will be vacuum impregnated with a second silver impregnation solution containing both the silver oxalate amine solution and the catalyst promoters. The second impregnation solution will be composed of all of the drained solution from the first impregnation plus a fresh aliquot of the first solution, or a new solution will be used. The promoters, in either aqueous solution or neat form, will be added (in the ascending numeric order listed in Table VI) with stirring in order to solubilize them, and will be added in sufficient amounts to reach the desired target levels on the finished catalysts. Two molar equivalents of diammonium EDTA will be added with the manganese promoter in order to increase the stability of the manganese-containing ion in the impregnation solution. The impregnation, draining and roasting steps for this second impregnation will be carried out analogously to the first impregnation.

The twice-impregnated finished catalysts will again be weighed, and based upon the weight gain of the catalysts in the second impregnation, the weight percent of silver and the concentration of the promoters will be calculated. The promoter levels will be adjusted to shaped porous body surface area. The estimated results of these calculations are provided in Table VI. Due at least in part to the enhanced properties provided to the shaped porous bodies by the precursor alumina blend, catalysts prepared from the shaped porous bodies are expected to be capable of being impregnated with greater amounts of silver and the exemplary chosen promoters.

TABLE VI

Expected Catalyst Properties

| Catalyst ID | Ag (wt %) | Promoter 1 $(NH_4)_2SO_4$ (ppm) | Promoter 2 CsOH (ppm) | Promoter 3 $Mn(NO_3)_2$ (ppm) | Promoter 4 $(NH_4)_2ReO_4$ |
| --- | --- | --- | --- | --- | --- |
| K<br>100 wt % CatD<br>(Comparative) | ~35 | ~150 $SO_4$ | ~600 Cs | ~50 Mn | ~250 Re |
| L<br>100 wt % CatD<br>70:30<br>Particle size<br>50µ:1µ | Comp value + ≥0.5 | Comp value + ≥10 | Comp value + ≥10 | Comp value + ≥5 | Comp value + ≥10 |
| M<br>100 wt % CatD<br>40:30:30<br>Particle size<br>100µ:50µ:1µ | Comp value + ≥0.5 | Comp value + ≥10 | Comp value + ≥10 | Comp value + ≥5 | Comp value + ≥10 |
| N<br>1:1:1<br>CatD:CatB:A-300 | Comp value + ≥0.5 | Comp value + ≥10 | Comp value + ≥10 | Comp value + ≥5 | Comp value + ≥10 |
| O<br>3:1:1<br>CatD:CatB:V-250 | Comp value + ≥0.5 | Comp value + ≥10 | Comp value + ≥10 | Comp value + ≥5 | Comp value + ≥10 |
| P<br>1:1:1:1<br>CatD:CatB:V-250:A-300 | Comp value + ≥0.5 | Comp value + ≥10 | Comp value + ≥10 | Comp value + ≥5 | Comp value + ≥10 |

C. Use of Inventive and Comparative Catalysts Prepared According to 2.8 to Catalyze Ethylene Epoxide Reactions A single-pass tubular reactor made of 0.25 inch OD stainless steel (wall thickness 0.035 inches) will be used for catalyst testing. The inlet conditions of the reactor that will be used are shown in Table VII.

TABLE VII

Ethylene Epoxidation Process Conditions

| Component | Oxygen Process Conditions-I Mole % |
|---|---|
| Ethylene | 30.0 |
| Oxygen | 8.0 |
| Ethane | 0.5 |
| Carbon Dioxide | 6.5 |
| Nitrogen | Balance of gas |
| Parts per million Ethyl Chloride | 3.5 |
| Type of Reactor | Tube |
| Amount of Catalyst | 0.5 g |

TABLE VII-continued

Ethylene Epoxidation Process Conditions

| Component | Oxygen Process Conditions-I Mole % |
|---|---|
| Total Outlet Flow Rate | 120 cc/min |

The pressure will be maintained constant at about 200 psig for the tube reactors. Ethyl chloride concentration will be adjusted to maintain maximum efficiency. Temperature (° C.) needed to produce 1.7 mole % ethylene oxide and catalyst efficiency (selectivity) at the outlet are typically measured and regarded as indicative of catalyst performance.

The catalyst test procedure is as follows: Approximately 5 g of catalyst will be crushed with a mortar and pestle, and then sieved to 30/50 U.S. Standard mesh. From the meshed material, 0.5 g will be charged to the reactor. Glass wool will be used to hold the catalyst in place. The reactor tube will be fitted into a heated brass block which has a thermocouple placed against it. The block will be enclosed in an insulated box. Feed gas will be passed over the heated catalyst at a pressure of 200 psig. The reactor flow will be adjusted and recorded at standard pressure and room temperature. Measurements of efficiency/selectivity and activity/temperature will be made under steady state conditions.

Table IV shows the expected temperature and selectivity as the total cumulative production of the reactor increases over time.

TABLE IV

| Catalyst | K<br>100 wt % CatD<br>(Comparative) | L<br>100 wt % CatD<br>70:30<br>Particle size<br>50μ:1μ | M<br>100 wt % CatD<br>40:30:30<br>Particle size<br>100μ:50μ:1μ | N<br>1:1:1<br>CatD:CatB:A-<br>300 | O<br>3:1:1<br>CatD:CatB:V-<br>250 | P<br>1:1:1:1<br>CatD:CatB:V-<br>250:A-300 |
|---|---|---|---|---|---|---|
| Day 18 (~8 Mlb EO/CF) | | | | | | |
| Selectivity (%) | ~82 | Comp value + ≥0.1 | Comp value + ≥0.1 | Comp value + ≥0.1 | Comp value + ≥0.1 | Comp value + ≥0.1 |
| Temperature (C.) | ~243 | Comp value − ≥0.1 | Comp value − ≥0.1 | Comp value − ≥0.1 | Comp value − ≥0.1 | Comp value − ≥0.1 |
| Day 27 (~16 Mlb EO/CF) | | | | | | |
| Selectivity (%) | ~82 | Comp value + ≥0.1 | Comp value + ≥0.1 | Comp value + ≥0.1 | Comp value + ≥0.1 | Comp value + ≥0.1 |
| Temperature (C.) | 247.7 | Comp value − ≥0.1 | Comp value − ≥0.1 | Comp value − ≥0.1 | Comp value − ≥0.1 | Comp value − ≥0.1 |
| Day 59 (~24 Mlb EO/CF) | | | | | | |
| Selectivity (%) | ~82 | Comp value + ≥0.1 | Comp value + ≥0.1 | Comp value + ≥0.1 | Comp value + ≥0.1 | Comp value + ≥0.1 |
| Temperature (C.) | 252.3 | Comp value − ≥0.1 | Comp value − ≥0.1 | Comp value − ≥0.1 | Comp value − ≥0.1 | Comp value − ≥0.1 |

We claim:

1. A process for making shaped porous bodies comprising:
   (a) selecting a blend of precursor aluminas that will provide the shaped porous bodies having at least one enhanced property as compared to the shaped porous bodies without the blend;
   (b) combining the selected precursor aluminas to provide porous body precursors; and
   (c) drying and calcining the porous body precursors to provide shaped porous bodies.

* * * * *